United States Patent
Xie et al.

(10) Patent No.: US 8,541,337 B2
(45) Date of Patent: *Sep. 24, 2013

(54) QUATERNARY OXIDES AND CATALYSTS CONTAINING QUATERNARY OXIDES

(75) Inventors: Rong-Cai Xie, Anqing (CN); Jian-Ku Shang, Mahomet, IL (US); Pinggui Wu, Tonawanda, NY (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/978,255

(22) Filed: Dec. 23, 2010

(65) Prior Publication Data

US 2011/0091514 A1   Apr. 21, 2011

Related U.S. Application Data

(63) Continuation of application No. 11/615,711, filed on Dec. 22, 2006, now Pat. No. 7,901,660.

(60) Provisional application No. 60/754,679, filed on Dec. 29, 2005.

(51) Int. Cl.
*B01J 23/00* (2006.01)
*B01J 27/24* (2006.01)
*B01J 21/02* (2006.01)
*B01J 27/02* (2006.01)
*B01J 27/135* (2006.01)

(52) U.S. Cl.
USPC ........... 502/350; 502/200; 502/202; 502/216; 502/227

(58) Field of Classification Search
USPC .............. 423/598, 277–280, 385, 415.1, 464, 423/518, 610; 502/350, 341, 325, 337, 345, 502/302, 303, 339, 344, 200, 202, 216, 227
See application file for complete search history.

(56) References Cited

U.S. PATENT DOCUMENTS

| | | | |
|---|---|---|---|
| 5,064,629 A | * | 11/1991 | Asaoka .................... 423/279 |
| 5,227,053 A | | 7/1993 | Brym |
| 5,326,633 A | | 7/1994 | Clough et al. |

(Continued)

FOREIGN PATENT DOCUMENTS

| EP | 1 314 477 A1 | 5/2003 |
|---|---|---|
| EP | 1354854 A1 | 10/2003 |

(Continued)

OTHER PUBLICATIONS

International Search Report and Written Opinion dated Oct. 19, 2010 for PCT Application No. PCT/US2010/022580.

(Continued)

*Primary Examiner* — Anthony J Zimmer
(74) *Attorney, Agent, or Firm* — Brinks Hofer Gilson & Lione

(57) ABSTRACT

A quaternary oxide includes a dopant metal, a dopant nonmetal, titanium, and oxygen. The atomic ratio of titanium, oxygen and dopant nonmetal may be 1:0.5-1.99:0.01-1.5. Quaternary oxides may be used in catalytic compositions, in coatings for disinfecting surfaces and in coatings for self-cleaning surfaces. A method of making a quaternary oxide includes combining ingredients including a titanium source, a dopant nonmetal source, a dopant metal salt, and a polar organic solvent to form a reaction mixture; and heating the reaction mixture.

19 Claims, 12 Drawing Sheets

(56) References Cited

U.S. PATENT DOCUMENTS

| | | | |
|---|---|---|---|
| 5,345,028 A * | 9/1994 | Alerasool | 585/730 |
| 5,462,674 A | 10/1995 | Butters et al. | |
| 5,554,300 A | 9/1996 | Butters et al. | |
| 5,589,078 A | 12/1996 | Butters et al. | |
| 5,597,515 A * | 1/1997 | Kauffman et al. | 252/519.12 |
| 6,136,203 A | 10/2000 | Butters et al. | |
| 6,162,530 A | 12/2000 | Xiao et al. | |
| 6,215,126 B1 | 4/2001 | Butters et al. | |
| 6,306,343 B1 | 10/2001 | Sugiyama | |
| 6,329,058 B1 | 12/2001 | Arney et al. | |
| 6,398,971 B1 | 6/2002 | Butters et al. | |
| 6,413,581 B1 | 7/2002 | Greenberg et al. | |
| 6,613,300 B2 | 9/2003 | Mangold et al. | |
| 6,673,433 B1 | 1/2004 | Saeki et al. | |
| 6,809,145 B1 | 10/2004 | Okamura et al. | |
| 6,835,688 B2 | 12/2004 | Morikawa | |
| 7,071,139 B2 | 7/2006 | Gole | |
| 7,138,357 B2 * | 11/2006 | Karvinen et al. | 502/216 |
| 7,232,556 B2 | 6/2007 | Yadav | |
| 7,901,660 B2 | 3/2011 | Xie et al. | |
| 2002/0006865 A1 | 1/2002 | Morikawa et al. | |
| 2002/0121206 A1 | 9/2002 | Ooishi | |
| 2003/0013607 A1 | 1/2003 | Morikawa et al. | |
| 2003/0050196 A1 | 3/2003 | Hirano et al. | |
| 2003/0052310 A1 | 3/2003 | Michot et al. | |
| 2003/0106488 A1 | 6/2003 | Huang et al. | |
| 2003/0166765 A1 | 9/2003 | Sugihara | |
| 2003/0171446 A1 | 9/2003 | Murrer et al. | |
| 2003/0196966 A1 | 10/2003 | Hughes | |
| 2003/0216252 A1 | 11/2003 | Gole | |
| 2004/0058149 A1 | 3/2004 | Zhou et al. | |
| 2004/0126624 A1 | 7/2004 | Akbar et al. | |
| 2004/0265587 A1 | 12/2004 | Koyanagi et al. | |
| 2005/0202241 A1 | 9/2005 | Shang et al. | |
| 2006/0078726 A1 | 4/2006 | Antonio et al. | |
| 2006/0254461 A1 | 11/2006 | Hong et al. | |
| 2007/0190765 A1 | 8/2007 | Xie et al. | |
| 2007/0202334 A1 | 8/2007 | Xie et al. | |
| 2010/0193449 A1 | 8/2010 | Shang et al. | |

FOREIGN PATENT DOCUMENTS

| | | |
|---|---|---|
| EP | 1 366 811 A1 | 12/2003 |
| EP | 1 411 033 | 4/2004 |
| EP | 1 449 811 A1 | 8/2004 |
| EP | 1 726 567 A1 | 11/2006 |
| JP | 11279453 A2 | 10/1999 |
| JP | 2002/030416 A2 | 1/2002 |
| JP | 2003137549 | 5/2003 |
| JP | 2004 130429 | 4/2004 |
| WO | WO 2004/007070 A1 | 1/2004 |
| WO | WO 2005/090236 A1 | 9/2005 |
| WO | WO 2007/059573 | 5/2007 |
| WO | WO 2007/117332 | 10/2007 |
| WO | WO 2007/117332 A2 | 10/2007 |
| WO | WO 2008/005055 A2 | 1/2008 |
| WO | WO 2009/086006 | 7/2009 |
| WO | WO 2010/088513 | 8/2010 |

OTHER PUBLICATIONS

Akikusa et al., "Photoelectrolysis of water to hydrogen in p-SiC/Pt and p-SiC/n-TiO$_2$ cells," International Journal of Hydrogen Energy, 27, pp. 863-870, 2002.

Anpo et al., "The design and development of highly reactive titanium oxide photocatalysts operating under visible light irradiation," Journal of Catalysis, 216, pp. 505-516, 2003.

Armstrong et al., "TiO$_2$-B Nanowires," Angew. Chem. Int. Ed., 43, pp. 2286-2288, 2004.

Bak et al., "Photo-electrochemical hydrogen generation from water using solar energy. Materials-related aspects," International Journal of Hydrogen Energy, 27, pp. 991-1022, 2002.

Lee et al., "Structural and Morphological Behavior of TiO$_2$ Rutile Obtained by Hydrolysis Reaction of Na$_2$Ti$_3$O$_7$," Bull. Korean Chem. Soc., vol. 25, No. 7, pp. 1051-1054, 2004.

Cai et al., "Induction of Cytotoxicity by Photoexcited TiO$_2$ Particles," Cancer Research, 52, pp. 2346-2348, 1992.

Mohler et al., "Cancer cell motility-inhibitory protein in the Dunning adenocarcinoma model," Cancer Research, vol. 52, pp. 2349-2352, 1992.

Yuan et al., "Hierarchical interlinked structure of titanium oxide nanofibers," Chem. Commun., pp. 1202-1203, 2002.

Chemseddine et al., "Nanostructuring Titania: Control over Nanocrystal Structure, Size, Shape, and Organization," Eur. J. Inorg. Chem., pp. 235-245, 1999.

Cozzoli et al., "Low-Temperature Synthesis of Soluble and Processable Organic-Capped Anatase TiO$_2$ Nanorods," J. Am. Chem. Soc., 125, pp. 14539-14548, 2003.

Deb, "Dye-sensitized TiO$_2$ thin-film solar cell research at the National Renewable Energy Laboratory (NREL)," Solar Energy Materials & Solar Cells, 88, pp. 1-10, 2005.

Fievet et al., "Preparing Monodisperse Metal Powders in Micrometer and Submicrometer Sizes by the Polyol Process," MRS Bulletin, pp. 29-34, 1989.

Fujihara et al., "Splitting of water by electrochemical combination of two photocatalytic reactions on TiO$_2$ particles," J. Chem. Soc., Faraday Trans., 94, pp. 3705-3709, 1998.

Bach et al., "Solid-state dye-sensitized mesoporous TiO$_2$ solar cells with high photon-to-electron conversion efficiencies," Nature, vol. 395, pp. 583-585, 1998.

Grätzel, "Photoelectrochemical cells," Nature, vol. 414, pp. 338-344, 2001.

Hadjiivanov et al., "Surface Chemistry of Titania (Anatase) and Titania-supported Catalysts," Chemical Society Reviews, pp. 61-69, 1996.

Huynh et al., "Hybrid Nanorod-Polymer Solar Cells," Science, vol. 295, pp. 2425-2427, 2002.

Jana, "Shape Effect in Nanoparticle Self-Assembly," Angew. Chem., 116, pp. 1562-1566, 2004.

Jiang et al., "Ethylene glycol-mediated synthesis of metal oxide nanowires," J. Mater. Chem., 14, pp. 695-703, 2004.

Jun et al., "Surfactant-Assisted Elimination of a High Energy Facet as a Means of Controlling the Shapes of TiO$_2$ Nanocrystals," J. Am. Chem. Soc., 125, pp. 15981-15985, 2003.

Lei et al., "Preparation and photoluminescence of highly ordered TiO$_2$ nanowire arrays," Applied Physics Letters, vol. 78, No. 8, pp. 1125-1127, 2001.

Li et al., "Shape Effects on Electronic States of Nanocrystals," Nano Letters, vol. 3, No. 10, pp. 1357-1363, 2003.

Phonthammachai et al., "Structural and rheological aspect of mesoporous nanocrystalline TiO$_2$ synthesized via sol-gel process," Microporous and Mesoporous Materials, 66, pp. 261-271, 2003.

Paunesku et al., "Biology of TiO$_2$-oligonucleotide nanocomposites," Nature Materials, vol. 2, pp. 343-346, 2003.

Anpo, "Utilization of TiO$_2$ photocatalysts in green chemistry," Pure Appl. Chem., vol. 72, No. 7, pp. 1265-1270, 2000.

Purifics "Photo-Cat Water Treatment," located at www.Purifics.com, 2 pages, 2005.

Smested, "Dye sensitized and organic solar cells," Solar Energy Materials & Solar Cells, 76, pp. 1-2, 2003.

Sugimoto, "Formation of Monodispersed Nano- and Micro-Particles Controlled in Size, Shape, and Internal Structure," Chem. Eng. Technol., 26, 3, pp. 313-321, 2003.

Sugimoto et al., "Synthesis of uniform anatase TiO$_2$ nanoparticles by gel-sol method 4. Shape control," Journal of Colloid and Interface Science, 259, pp. 53-61, 2003.

Sun et al., "Large-Scale Synthesis of Uniform Silver Nanowires Through a Soft, Self-Seeding, Polyol Process," Adv. Mater. 14, No. 11, pp. 833-837, 2002.

Trentler et al., "Synthesis of TiO$_2$ Nanocrystals by Nonhydrolytic Solution-Based Reactions," J. Am. Chem. Soc., 121, pp. 1613-1614, 1999.

Wang et al., "A Solution-Phase, Precursor Route to Polycrystalline SnO$_2$ Nanowires That Can Be Used for Gas Sensing under Ambient Conditions," J. Am. Chem. Soc., 125, pp. 16176-16177, 2003.

Wang et al., "Single Crystalline Nanowires of Lead: Large-Scale Synthesis, Mechanistic Studies, and Transport Measurements," J. Phys. Chem. B, 108, pp. 8631-8640, 2004.

Liu et al., "Preparation and Properties of Nanostructure Anatase $TiO_2$ Monoliths Using 1-Butyl-3-methylimidazolium Tetrafluoroborate Room-Temperature Ionic Liquids as Template Solvents," Crystal Growth & Design, vol. 5, No. 4, pp. 1643-1649, 2005.

Zhang et al., "Hydrothermal preparation of porous nano-crystalline $TiO_2$ electrodes for flexible solar cells," Journal of Photochemistry and Photobiology A: Chemistry, 164, pp. 159-166, 2004.

Zhang et al., "Preparation of Oxide Nanocrystals with Tunable Morphologies by the Moderate Hydrothermal Method: Insights from Rutile $TiO_2$," Langmuir, 19, pp. 967-971, 2003.

Curtis et al., "Morphology Control in the Hydrothermal Synthesis of Nanostructured Titanium Oxides," Abstract Y2.3, p. 540, in Symposium Y, Solvothermal Synthesis and Processing of Materials, vol. 878E, pp. 537-547, 2005.

Hydroxyl Systems, "Advanced Oxidation Technologies," located at www.hydroxyl.com/, 1 page, printed Jun. 28, 2005.

SITE, "Matrix Photocatalytic Inc.," pp. 86-89, 2007.

Process Technologies Inc., "Alternative Treatment Technologies, $TiO_2$ Photocatalytic Destruction—Matrix Photocatlytic Inc.," located at http://sve.ucdavis.edu/MatrixPCOSummary.htm, 1 page, printed Dec. 9, 2005.

Process Technologies Inc., "$TiO_2$ Photocatalytic Destruction-(Matrix Photocatlytic)," located at http://sve.ucdavis.edu/MatrixPCORprt.htm, 11 pages, printed Dec. 9, 2005.

Fujishima et al., "Titanium dioxide photocatalysis," Journal of Photochemistry and Photobiology C: Photochemistry Reviews, 1, pp. 1-21, 2000.

Intentionally Left Blank.

Meier et al., "Redox Targeting of Oligonucleotides Anchored to Nanocrystalline $TiO_2$ Films for DNA Detection," Chemphyschem, 4, pp. 371-374, 2002.

Kubota et al., "Application of photoexcited $TiO_2$ particle to regional cancer treatment: a new approach," Reg. Cancer Treat., vol. 8, pp. 192-197, 1995.

Dunlop et al., "The photocatalytic removal of bacterial pollutants from drinking water," Journal of Photochemistry and Photobiology A: Chemistry, 148, pp. 355-363, 2002.

Duonghong et al., "Integrated Systems for Water Cleavage by Visible Light; Sensitization of $TiO_2$ Particles by Surface Derivatization with Ruthenium Complexes," Helvetica Chimica Acta, 67, pp. 1012-1018, 1984.

Kobayashi et al., "Preparation of $TiO_2$ Hollow-Fibers Using Supramolecular Assemblies," Chem. Mater., 12, 6, pp. 1523-1525, 2000.

Invitation to Pay Additional Fees dated Oct. 29, 2007 for PCT Application No. PCT/US2006/062571.

Cheng, P. et al., "Recent Progress in Titania Photocatalyst Operating Under Visible Light", Progress In Chemistry, vol. 17, No. 1, pp. 8-14, (2005).

Huang, W. et al., "Progress of Semiconductor Phogocatalysts Under Visible Light Irradiation", Progress In Chemistry, vol. 17, No. 2, pp. 242-247, (2005).

Lin, L. et al, "Phosphor-doped Titania—a Novel Photocatalyst Active in Visible Light", Chemistry Letters, vol. 34 No. 3, pp. 284-285, (2005).

Ohno, T. et al., "Preparation of S-doped $TiO_2$ photocatalysts and their photocatalytic activities under visible light", Applied Catalysis A: General, 265, pp. 115-121, (2004).

Reddy, E.P. et al., "Transition Metal Modified $TiO_2$-Loaded MCM-41 Catalysts for Visible- and UV-Light Driven Photodegradation of Aqueous Organic Pollutants", Journal of Physical Chemistry B, 108, pp. 17198-17205, (2004).

Wu, P.G. et al. "Effects of nitrogen doping on optical properties of $TiO_2$ thin films", Applied Physics, A81, pp. 1411-1417, (2005).

Yu, J.C. et al., "Efficient Visible-Light-Induced Photocatalytic Disinfection on Sulfur-Doped Nanocrystalline Titania", Environmental Science & Technology, 39, pp. 1175-1179, (2005).

Sakatani, Y. et al., "Photocatalytic Decompsotion of Acetaldehyde under Visible Light Irradiation over $La^{3+}$ and N Co-doped $TiO_2$", Chemistry Letters, vol. 32, No. 12, pp. 1156-1157, (2003).

Sakatani, Y. et al., "Metal ion and N co-doped $TiO_2$ as a visible-light photocatalyst", J. Materials Research., vol. 19, No. 7, pp. 2100-2108, (2004).

Li, L. et al., "Photocatalytic oxidation and ozonation of catechol over carbon-black-modified nano-$TiO_2$ thin films supported on A1 sheet", Water Research, 37, pp. 3646-3651, (2003).

Rampaul, A. et al., "Titania and tungsten doped titania thin films on glass; active photocatalysts", Polyhedron, 22, pp. 35-44, (2003).

Langlet, M. et al., "Sol-Gel Preparation fo Photocatalytic $TiO_2$ Films on Polymer Substrates" Journal of Sol-Gel Science and Technology, 25, pp. 223-234, (2002).

Belhacova, L. et al. "Inactivation of microorganisms in a flow-through photoreactor with an immobilized $TiO_2$ layer", Journal of Chemical Technology and Biotechnology, 74, pp. 149-154, (1999).

Yu, M.J. et al., "Photocatalytic Cell Disruption of *Giardia lamblia* in a UV/$TiO_2$ Immobilized Optical-Fiber Reactor", Journal of Microbiology and Biotechnology, 14(6), pp. 1105-1113, (2004).

Choi, Y.S. et al., "Photocatalytic disinfection of *E coli* in a UV/$TiO_2$-immobilised optical-fibre reactor", Journal of Chemical Technology and Biotechnology, 75, pp. 1145-1150, (2000).

Shchukin, D.G., "Heterogeneous photocatalysis in titania-containing liquid foam", Photochemical & Photobiological Sciences, 3, pp. 157-159, (2004).

Gracia, F. et al., "Structural, Optical, and Photoelectrochemical Properties of $M^{n+}$—$TiO_2$ Model Thin Film Photocatalysts", Journal of Physical Chemistry B, 108, pp. 17466-17476, (2004).

Litter, M.I., "Heterogeneous photocatalysis Transition metal ions in photocatalytic systems", Applied Catalysis B: Environmental, 23, pp. 89-114, (1999).

Sunada, K. et al., "Bactericidal Activity of Copper-Deposited $TiO_2$ Think Film under Weak UV Light Illumination", Environmental Science & Technology, 37, pp. 4785-4789, (2003).

Tatsuma, T. et al., "Bactericidal effect of an energy storage $TiO_2$-$WO_3$ photocatalyst in dark", Electrochemistry Communications, 5, pp. 793-796, (2003).

Fuerte, A. et al., "Visible light-activated nanosized doped-$TiO_2$ photocatalysts", Chemcomm Communication, pp. 2718-2719, (2001).

Selcuk, H. et al., "Photocatalytic and photoelectrocatalytic performance of 1% Pt doped $TiO_2$ for the detoxification of water", Journal of Applied Electrochemistry, 34, pp. 653-658, (2004).

Matsunaga, T. et al., "Photoelectrochemical sterilization of microbial cells by semiconductor powders", FEMS Microbiology Letters, 29, pp. 211-214, (1985).

Li, W. et al., "Band gap tailoring of $Nd^3$-doped $TiO_2$ nanoparticles", Applied Physics Letters, vol. 83, No. 20, pp. 4143-4145, (2003).

Yan, X. et al., "Preparation, characterization and photocatalytic activity of Si-doped and rare earth-doped $TiO_2$ from mesoporous precursors", Appl. Catalysis B: Environmental 55, pp. 243-252, (2005).

Iwasaki, M. et al., "Cobalt Ion-Doped $TiO_2$ Photocatalyst Response to Visible Light", Journal of Colloid & Interface Science, 224, pp. 202-204 (2000).

Ruiz, A. et al., "Study of the influence of Nb content and sintering temperature on $TiO_2$ sensing films", Thin Solid Films, 436, pp. 90-94, (2003).

M. Sökmen, et al., "Disinfection of *E. coli* by the Ag-$TiO_2$/UV system: lipidperoxidation", Journal of Photochemistry and Photobiology A:Chemistry, 143, pp. 241-244, (2001).

Belver, C, et al., "Palladium enhanced resistance to deactivation of titanium dioxide during the photocatalytic oxidation of tolune vapors", Applied Catalysis B: Environmental, 46, pp. 497-509, (2003).

International Search Report and Written Opinion dated Feb. 19, 2008 for PCT Application No. PCT/US2006/062571.

Invitation to Pay Additional Fees dated Jan. 23, 2008 for PCT Application No. PCT/US2006/062576.

Yoshida, R. et al., "Syntheses of $TiO_2$ nanowires and $TiO_2$ anatase nanowires by hydrothermal and post-heat treatments", Journal of Solid State Chemistry, 178, pp. 2179-2185, (2005).

Seo, D.S. et al., "Preparation of nanotube-shaped $TiO_2$ powder" Journal of Crystal Growth, 229, pp. 428-432 (2001).

Cai, R. et al., "Photokilling of malignant cells with ultrafine $TiO_2$ Powder", The Chemical Society of Japan, vol. 64, No. 4, pp. 1268-1273, (1991).

Wu, P. G. et al., "Visible-light photocatalytic fibers for inactivation of pseudomonas aeruginosa" Advances in Bioceramics and Biocomposites II., Ceramic Engineering and Science Proceedings, vol. 27, issue 6, pp. 111-119, (2008).

Yuan, Z-Y. et al., "Titanium oxide nanotubes, nanofibers and nanowires", Colloids and Surfaces: A Physicochem, Eng. Aspects, vol. 241, pp. 173-183, (2004).

Wu, P. et al., "Enhanced visible-light photocatalytic disinfection of bacterial spores by palladium-modified nitrogen-doped titanium oxide", Journal of the American Ceramic Society, vol. 91, Issue 9, pp. 2957-2962, (2008).

Li, Q. et al., "Palladium oxide nanoparticles on nitrogen-doped titanium oxide: Accelerated photocatalytic disinfection and post-illumination catalytic "memory"", Advanced Materials, vol. 20, issue 19, pp. 3717-3723, (2008).

Li, Q. et al., "As(III) Removal by palladium-modified nitrogen-doped titanium oxide nanoparticle photocatalyst", Environmental Science & Technology, vol. 43, No. 5, pp. 1534-1539, (2009).

Nordstrom, D.K. "Worldwide occurrences of arsenic in ground-water", Science, vol. 296, pp. 2143-2144, (2002).

Amini, M. et al., "Statistical modeling of global geogenic arsenic contamination in groundwater", Environmental Science & Technology, vol. 42, pp. 3669-3675, (2008).

Welch, A.H. et al., "Arsenic in ground water of the United States: occurrence and geochemistry", Ground Water, vol. 38, pp. 589-604, (2000).

Smedley, P.L. et al., "A review of the source, behaviour and distribution of arsenic in natural waters", Appl. Geochem., vol. 17, pp. 517-568, (2002).

Smith, A.H., et al., "Contamination of drinking-water by arsenic in Bangladesh: a public health emergency", Bull. World Health Org., vol. 78, pp. 1093-1103, (2000).

Rich, C.H., et al., "Lung and kidney cancer mortality associated with arsenic in drinking water in Cordoba", Argentina. Int. Epidemiol., vol. 27, pp. 561-569, (1998).

Xia, Y., et al., "An overview on chronic arsenism via drinking water in PR China", Toxicology, vol. 198, pp. 25-29, (2004).

Saha, K.C., "Review of Arsenicosis in West Bengal, India—A clinical perspective" Critical Review Environmental Science & Technology, vol. 30, pp. 127-163, (2003).

Smith, A.H., et al., "Arsenic epidemiology and drinking water standards", Science, vol. 296, pp. 2145-2146, (2002).

U.S. Environmental Protection Agency. Technologies and Costs for Removal of Arsenic from Drinking Water, Washington, DC, 2000.

Dixit, S., et al., "Comparison of arsenic(V) and arsenic (III) sorption onto iron oxide minerals: implications for arsenic mobility", Environmental Science & Technology, vol. 37, pp. 4182-4189, (2003).

Borho, M., et al., "Optimized removal of arsenite(III) by adaptation of oxidation and precipitation processes to the filtration step", Water Science & Technology, vol. 34, pp. 25-31, (1996).

Lee, H., et al., "Photocatalytic oxidation of arsenite in TiO2 suspension: kinetics and mechanisms", Environmental Science & Technology, vol. 36, pp. 3872-3878, (2002).

Kim, Y., et al., "Arsenic removal using mesoporous alumina prepared via a templating method", Environmental Science & Technology, vol. 38, pp. 924-931, (2004).

Edwards, M., "Chemistry of arsenic removal during coagulation and Fe-Mn oxidation", Journal of the American Water Works Association, pp. 64-78, (1994).

McNeil, L.S., et al., "Soluble arsenic removal at watertreatment plants", Journal of the American Water Works Association, pp. 105-113, (1995).

Hering, J.G., et al., "Arsenic removal by ferric chloride", Journal of the American Water Works Association, pp. 155-167, (1996).

Pande, S.P., et al., "Arsenic removal studies in some ground waters of west Bengal, India", Journal of Environmental Science & Health, vol. 32, pp. 1981-1987, (1997).

Kim, M., et al., "Oxidation of arsenite in groundwater using ozone and oxygen", Science Total Environment, vol. 247, pp. 71-79, (2000).

Pettine, M., et al., "Arsenite oxidation by H2O2 in aqueous solutions", Geochem. Cosmochim. Acta, vol. 63, pp. 2727-2735, (1999).

Dodd, M.C., et al., "Kinetics and mechanistic aspects of As(III) oxidation by aqueous chlorine, chloramines, and ozone: relevance to drinking water treatment", Environmental Science & Technology, vol. 40, pp. 3285-3292, (2006).

Scott, M.J., et al., "Reactions at oxide surfaces. 1. Oxidation of As(III) by synthetic bimessite", Environmental Science & Technology, vol. 29, pp. 1898-1905, (1995).

Chiu, V.Q., et al., "Arsenic adsorption and oxidation at Manganite surfaces. 1. Method for simultaneous determination of adsorbed and dissolved arsenic species", Environmental Science & Technology, vol. 34, pp. 2029-2034, (2000).

Yang, H., et al., "Homogeneous and hetero geneous photocatalytic reactions involving As(III) and As(V) species in aqueous media", Journal of Photochemical & Photobiology A, vol. 123, pp. 137-143, (1999).

Emett, M.T., et al., "Photochemical oxidation of arsenic by oxygen and iron in acidic solutions", Water Research, vol. 35, pp. 649-656, (2001).

Hug, S.J., et al., "Solar oxidation and removal of arsenic at circumneutral pH in iron containing waters", Environmental Science & Technology, vol. 35, pp. 2114-2121, (2001).

Kocar, B.D., et al., "Photochemical oxidation of As(III) in ferrioxalate solutions", Environmental Science & Technology, vol. 37, pp. 1581-1588, (2003).

Hug, S.J., et al., "Iron-catalyzed oxidation of arsenic (III) by oxygen and by hydrogen peroxide: pH-dependent formation of oxidants in the Fenton reaction", Environmental Science & Technology, vol. 37, pp. 2734-2742, (2003).

Ryu, J., et al., "Effects of TiO2 surface modifications on photocatalytic oxidation of arsenite: the role of superoxides", Environmental Science & Technology, vol. 38, pp. 2928-2933, (2004).

Ferguson, M.A., et al., "Ti02-photo-catalyzed As(III) oxidation in aqueous suspensions: Reaction kinetics and effects of adsorption", Environmental Science & Technology, vol. 39, pp. 1880-1886, (2005).

Dutta, P.K., et al., "Photocatalytic oxidation of arsenic(III): Evidence of hydroxyl radicals", Environmental Science & Technology, vol. 39, pp. 1827-1834, (2005).

Nakajima, T., et al., "Combined use of photocatalyst and aadsorbent for the removal of inorganic arsenic(III) and organoarsenic compounds from aqueous media", Journal of Hazard. Materials B, vol. 120, pp. 75-80, (2005).

Yoon, S.H., et al., "Oxidation mechanism of As(III) in the UV/TiO2 system: evidence for a direct hole oxidation mechanism", Environmental Science & Technology, vol. 39, pp. 9695-9701, (2005).

Ferguson, M.A., et al., "Ti02-photocatalyzed As(III) oxidation in a fixed-bed, flow-through reactor", Environmental Science & Technology, vol. 40, pp. 4261-4267, (2006).

Asahi, R., et al., "Visible-light photocatalysis in nitrogen-doped titanium oxides", Science, vol. 293, pp. 269-271, (2001).

Khan, S.U.M., et al., "Efficient photo-chemical water splitting by a chemically modified n-TiO2", Science, vol. 297, pp. 2243-2245, (2002).

Li, Q., et al.,"Enhanced visible-light absorption from PdO nanoparticles in nitrogen-doped titanium oxide thin films", Applied Physical Letters, vol. 90, 063109, (2007).

Li, Q., et al., "Enhanced visible-light photocatalytic degradation of humic acid by palladium oxide-sensitized nitrogen-doped titanium oxide", Journal of American Ceramics Society, vol. 90, pp. 3863-3868, (2007).

Dutta, P.K., et al.,"Adsorption of arsenate and arsenite on titanium dioxide suspensions", Journal of Colloid Interface Science, vol. 278, pp. 270-275, (2004).

Bang, S., et al.,"Removal of arsenic from groundwater by granular titanium dioxide adsorbent", Chemosphere, vol. 60, pp. 389-397, (2005).

Jing, C., et al.,"Arsenic leachability in water treatment adsorbents", Environmental Science & Technology, vol. 39, 5481-5487, (2005).

Pena, M.E., et al., "Adsorption of As(V) and As(III) by nanocrystalline titanium dioxide", Water Research, vol. 39, pp. 2327-2337, (2005).

Pena, M., et al., "Adsorption mechanism of arsenic on nanocrystalline titanium dioxide", Environmental Science & Technology, vol. 40, pp. 1257-1262, (2006).

Sag, Y., et al., "Kinetic studies on sorption of Cr(VI) and Cu(II) ions by chitin, chitosan and rhizopus arrhizus", Biochem. Eng., vol. 12, pp. 143-153, (2002).

Miyauchi, M., et al., "Zeta potential and photocatalytic activity of nitrogen doped TiO2 thin films", Phys. Chem. Chem. Phys., vol. 6, pp. 865-870, (2004).

Li, Q., et al., "Modulation of MS2 virus adsorption on TiO2 semiconductor film by nitrogen doping", Journal of Material Research, vol. 22, pp. 3036-3041, (2007).

Irie, H., et al., "Nitrogen-concentration dependence on photocatalytic activity of $TiO_{2-x}N_x$ powders", Journal of Physical Chemistry B, vol. 107, pp. 5483-5486, (2003).

Torres, G.R., et al., "Photoelectrochemical study of nitrogen-doped titanium dioxide for water oxidation", Journal of Physical Chemistry B, vol. 108, pp. 5995-6003, (2004).

International Search Report and Written Opinion dated Jun. 30, 2009 for PCT Application No. PCT/US2008/087523.

Wei, H. et al., "Preparation and photocatalysis of $TiO_2$ nanoparticles co-doped with nitrogen and lanthanum", Journal of Materials Science, 39, pp. 1305-1308, (2004).

Iliev, V. et al., "Photooxidation of xylenol orange in the presence of palladium-modified $TiO_2$ catalysts", Catalysis Communications, 5, pp. 759-763, (2004).

Kumar, S. et al., "Photodegradation of ethylene using visible light responsive surfaces prepared from titania nanoparticle slurries", Applied Catalysis B: Environmental, 57, pp. 93-107, (2005).

\* cited by examiner t = 0 t = 0.2 s t = 0.4 s t = 0.6 s

QUATERNARY OXIDES AND CATALYSTS CONTAINING QUATERNARY OXIDES

REFERENCE TO RELATED APPLICATIONS

This application is a continuation application of U.S. application Ser. No. 11/615,711, filed Dec. 22, 2006 now U.S. Pat. No. 7,901,660, which claims the benefit of U.S. Provisional Application No. 60/754,679 entitled "Quaternary Oxides And Catalysts Containing Quaternary Oxides" filed Dec. 29, 2005, which is incorporated by reference in its entirety.

FEDERALLY SPONSORED RESEARCH OR DEVELOPMENT

The subject matter of this application may have been funded in part under a research grant from the National Science Foundation, under Grant Number CTS-0120978, Banner/UFAS 149646919110. The U.S. Government may have rights in this invention.

BACKGROUND

Photocatalysts provide for catalysis of chemical reactions when irradiated by electromagnetic radiation. One advantage of photocatalysts is environmental stability, since they are relatively inert until subjected to irradiation. Photocatalysts have been investigated for applications in a variety of areas, including environmental remediation. Stable catalysts that promote oxidation reactions can oxidize pollutants in air and in water, including inorganic pollutants, organic pollutants and microorganisms. By breaking the pollutants down into substances that are less harmful, the need for storage or disposal of pollutants that have been extracted from air or water can be minimized.

Titanium oxide ($TiO_2$) in the anatase structure type is an example of a photocatalyst that is useful in many different applications. Titanium oxide is a semiconductor that is stable in a wide range of environmental conditions and that promotes oxidation-reduction (redox) reactions when irradiated with ultraviolet light. Systems utilizing titanium oxide and ultraviolet radiation have been used for commercial water purification. In addition, titanium oxide has been investigated and/or used for applications including air purification, hydrogen production by the photochemical splitting of water, nitrogen fixation, odor control, antimicrobial surface coatings, and self-cleaning surface coatings.

One drawback to the use of titanium oxide as a photocatalyst is the requirement for irradiation by ultraviolet light, due to its large band gap. Since ultraviolet radiation is only a small portion of solar radiation once it has passed though the atmosphere, titanium oxide has a low photon yield when exposed to sunlight. Doping of titanium oxide with other elements can provide for a narrowing of the band gap, allowing for increased reactivity under visible light. These doped materials do not necessarily provide for increased oxidation of pollutants under visible light, however. Possible explanations for the low oxidation efficiency include rapid recombination of the electron-hole pairs before oxidation can occur, and the short lifetimes of the charge carrying dopants. In addition, doped titanium oxide typically is expensive to produce and is difficult to obtain in large enough quantities for use in environmental remediation facilities.

A stable photocatalyst that can efficiently promote redox reactions under visible light would be beneficial. It would be desirable to form such a photocatalyst by a method that is relatively inexpensive and that can be readily scaled up to produce large quantities.

SUMMARY

In one aspect, the invention provides a quaternary oxide that includes a dopant metal, a dopant nonmetal, titanium, and oxygen. The atomic ratio of titanium, oxygen and dopant nonmetal is 1:0.5-1.99:0.01-1.5.

In another aspect of the invention, there is a catalytic composition that includes a quaternary oxide including a dopant metal, a dopant nonmetal, titanium and oxygen. The atomic ratio of titanium, oxygen and dopant nonmetal is 1:0.5-1.99: 0.01-1.5.

In yet another aspect of the invention, there is a disinfecting surface that includes a coating on a substrate, where the coating contains a quaternary oxide including a dopant metal, a dopant nonmetal, titanium and oxygen. When bacteria are in contact with the composition and are irradiated with visible light, the concentration of living bacteria is reduced by 20% within 1 hour.

In yet another aspect of the invention, there is a self-cleaning surface that includes a coating on a substrate, where the coating contains a quaternary oxide including a dopant metal, a dopant nonmetal, titanium and oxygen. When an organic substance is in contact with the coating and is irradiated with visible light, the concentration of the organic substance is reduced by 40% within 4 hours.

In yet another aspect of the invention, there is a method of making a quaternary oxide that includes combining ingredients to form a reaction mixture, and heating the reaction mixture. The ingredients include a titanium source, a dopant nonmetal source, a dopant metal salt, and a polar organic solvent.

In yet another aspect of the invention, there is a method of making a quaternary oxide that includes combining a titanium source and a dopant nonmetal source with a polar organic solvent to form a first mixture, adding a dopant metal salt to the first mixture to form a reaction mixture, heating the reaction mixture at a temperature of from 50° C. to 250° C. for a period of at least 4 hours, removing a precipitate from the reaction mixture, and calcining the precipitate.

In yet another aspect of the invention, there is a method of making a quaternary oxide that includes combining a polar organic solvent with a dopant nonmetal source to form a first mixture, adding a titanium source to the first mixture to form a second mixture, adding a dopant metal salt to the second mixture to form a reaction mixture and heating the reaction mixture in an autoclave at a temperature of from 100° C. to 350° C. for a period of at least 4 hours.

The following definitions are included to provide a clear and consistent understanding of the specification and claims.

The term "quaternary oxide" means a substance containing oxygen and at least three other elements.

The term "titanium source" means a substance containing titanium that is soluble in a solvent.

The term "dopant nonmetal" means a nonmetal element that is not oxygen; for example boron, carbon, nitrogen, fluorine, silicon, phosphorus, sulfur, chlorine, germanium, arsenic, selenium, bromine, antimony, tellurium, iodine or astatine.

The term "dopant nonmetal source" means a substance containing a nonmetal element that is not oxygen, and optionally containing other elements. For example, a dopant nonmetal source may contain boron, carbon, nitrogen, fluorine, silicon, phosphorus, sulfur, chlorine, germanium, arsenic, selenium, bromine, antimony, tellurium, iodine and/or astatine.

The term "dopant metal" means a metal element that is not titanium; for example, an element having an atomic number of 13, 20, 21, from 23 to 31, from 38 to 50, or from 56 to 83.

The term "dopant metal salt" means a substance containing a metal that is not titanium, and that can provide a source of ions of the metal, where the metal ion is an ion of an element having an atomic number of 13, 20, 21, from 23 to 31, from 38 to 50, or from 56 to 83. Dopant metal salts include, for example, salts of the metal and oxides of the metal.

The term "polar organic solvent" means a non-aqueous solvent having a dielectric constant at 25° C. of at least 10.

The term "calcination" means heating a substance at a temperature below its melting point, sufficient to cause growth of grains. Preferably the heating temperature is at least halfway between 0° C. and the melting temperature of the lowest melting component in the substance.

The term "photocatalysis" means a catalysis that is dependent on the presence of electromagnetic radiation to catalyze a reaction.

The term "visible light" means electromagnetic radiation having a wavelength of 380 nm to 780 nm.

The term "oxidation-reduction reaction" means a chemical reaction between two species involving the transfer of at least one electron from one species to the other species. This type of reaction is also referred to as a "redox reaction." The oxidation portion of the reaction involves the loss of at least one electron by one of the species, and the reduction portion involves the addition of at least one electron to the other species.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

The present invention makes use of the discovery that quaternary titanium oxides (titanium oxide doped with a metal and a nonmetal) may exhibit efficient photocatalysis of redox reactions. A small amount of dopant is sufficient to provide photocatalytic oxidation of organic compounds and bacteria, among other reactions. In addition, it has been discovered that titanium oxide may be doped with metals and/or nonmetals by methods that are less expensive than conventional doping methods and that can be performed on a large scale. These methods may be performed at relatively low temperatures, and the doped titanium oxide products may be coated onto a variety of surfaces.

A method of making a quaternary oxide includes heating a mixture of substances containing titanium, oxygen, a dopant nonmetal and a dopant metal. Other substances or elements may be present in the mixture, such as halides, hydrogen, etc., provided that they volatilize or phase separate from the mixture during heating. The titanium may be present in the mixture as an oxide, a sulfide, a halide, an alkoxide, a nitrate, and/or an oxysulfate. The oxygen may be present in the mixture as part of a compound with titanium, such as a titanium oxide, a titanium alkoxide, and/or a titanium oxysulfate. The dopant nonmetal may be present in the mixture as a hydrogen compound such as ammonia or an ammonium salt, ammonium bifluoride, a borohydride, or hydrogen sulfide. The dopant nonmetal may be present in the mixture as a metal compound such as a metal nitride, a metal sulfide, or a metal oxide. The dopant nonmetal may be present in the mixture as a component of a salt such as a sulfate or a carbonate. The dopant nonmetal may be present in the mixture as an organic compound, such as an amine, an alcohol, a carboxylic acid, an aldehyde, a ketone, a sulfone, a sulfoxide, or a fluorocarbon. The dopant metal may be present in the mixture as an oxide, a sulfide, a halide, an alkoxide, a nitrate, or an oxysulfate.

A variety of synthetic methods may be used, including conventional solid phase synthesis, sol-gel methods, solvothermal methods, etc. Preferably the components are intimately mixed prior to heating, such as by being dissolved in a common solvent or, when in the solid phase, by repeated grinding and heating.

Figure 1:
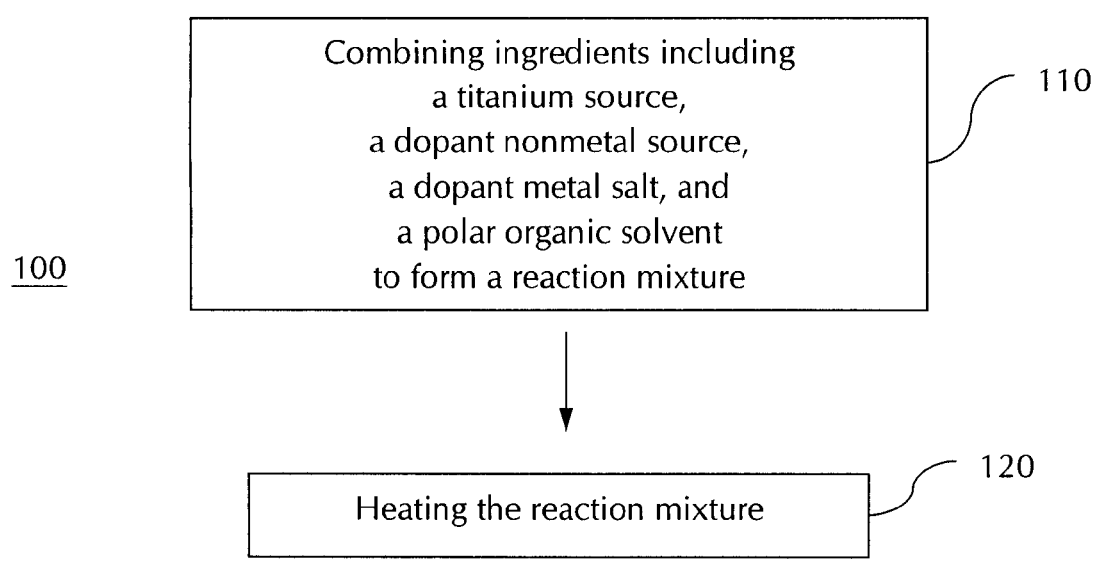
FIG. 1 depicts a method of making a quaternary oxide.

FIG. 1 represents an example of a solvothermal method 100 of making a quaternary oxide that includes combining ingredients including a titanium source, a dopant nonmetal source, a dopant metal salt, and a polar organic solvent to form a reaction mixture 110; and heating the reaction mixture 120. Combining ingredients 110 may include mixing the ingredients in any order. Combining ingredients 110 also may include adding other ingredients to form the reaction mixture. A quaternary oxide formed by the method may contain a dopant metal, a dopant nonmetal, titanium and oxygen.

The titanium source may be any titanium compound or complex, including an oxide, a sulfide, a halide, an alkoxide, a nitrate, and an oxysulfate. Preferably the titanium source is a titanium(IV) halide, a titanium(IV) alkoxide, a titanium(IV) nitrate or a titanium(IV) oxysulfate. More preferably the titanium source is a titanium(IV) alkoxide.

The dopant nonmetal source may be a hydrogen compound, a metal compound, a component of a salt, or an organic compound. Preferably the dopant nonmetal source includes boron, carbon, nitrogen, sulfur, fluorine, or a combination of these elements. More preferably the dopant nonmetal source includes nitrogen.

The dopant metal salt may be an oxide, a sulfide, a halide, an alkoxide, a nitrate, or an oxysulfate. Preferably the dopant metal salt contains an ion of calcium, cobalt, nickel, copper, gallium, strontium, yttrium, zirconium, palladium, silver, tin, lanthanum or platinum.

The polar organic solvent may be any non-aqueous solvent having a dielectric constant at 25° C. of at least 10. Preferably the polar organic solvent has a boiling point at one atmosphere pressure of at least 100° C. More preferably the polar organic solvent has a dielectric constant at 25° C. of at least 25 and a boiling point at one atmosphere pressure of at least 150° C. Preferably the polar organic solvent is ethylene glycol.

Other ingredients may include water, a surfactant, or a surface-directing agent. One or more of these other ingredients may be combined with the titanium source, dopant nonmetal source, and dopant metal salt to form the reaction mixture. One or more of these other ingredients may be combined with one or two of the titanium source, the dopant nonmetal source and dopant metal salt, and then combined with the remaining ingredient or ingredients to form the reaction mixture. One or more of these other ingredients may be added to the reaction mixture just prior to heating the reaction mixture.

Figure 2:
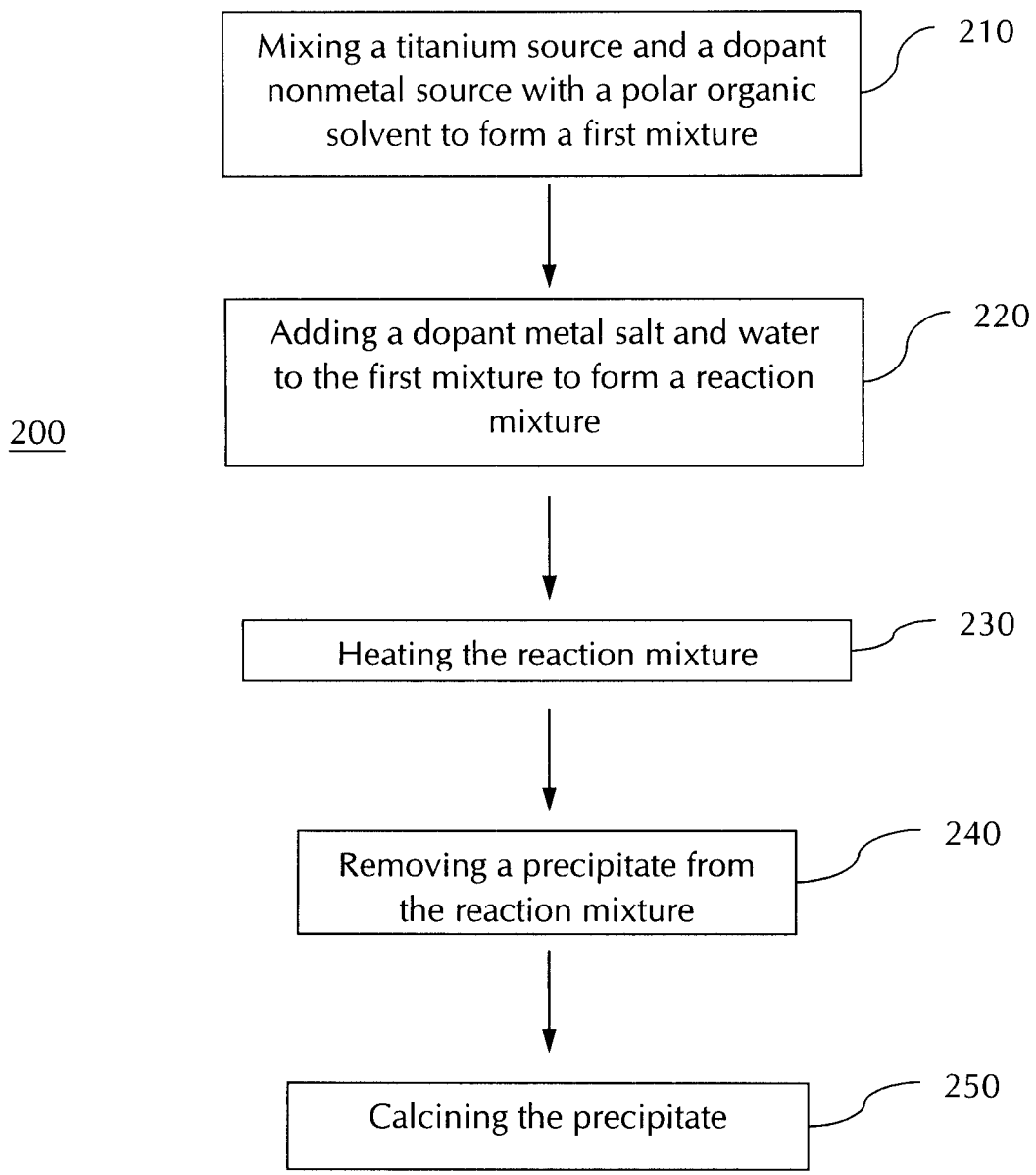
FIG. 2 depicts a method of making a quaternary oxide by a sol-gel procedure.

FIG. 2 represents a method 200 of making a quaternary oxide by a sol-gel procedure that includes mixing a titanium source and a dopant nonmetal source with a polar organic solvent to form a first mixture 210, adding a dopant metal salt and water to the first mixture to form a reaction mixture 220, heating the reaction mixture 230, removing a precipitate from the reaction mixture 240, and calcining the precipitate 250. Heating the reaction mixture 230 may include heating the reaction mixture at a temperature of from 50° C. to 250° C. for at a period of at least 4 hours. Preferably the reaction mixture is heated at a temperature of from 70° C. to 150° C. for a period of from 5 hours to 48 hours, and preferably at a temperature of from 70° C. to 150° C. for a period of at least 12 hours. Removing a precipitate from the reaction mixture may include conventional separation methods, such as filtration and/or centrifugation. The precipitate may include a quaternary oxide containing a dopant metal, a dopant nonmetal, titanium and oxygen.

Figure 3:
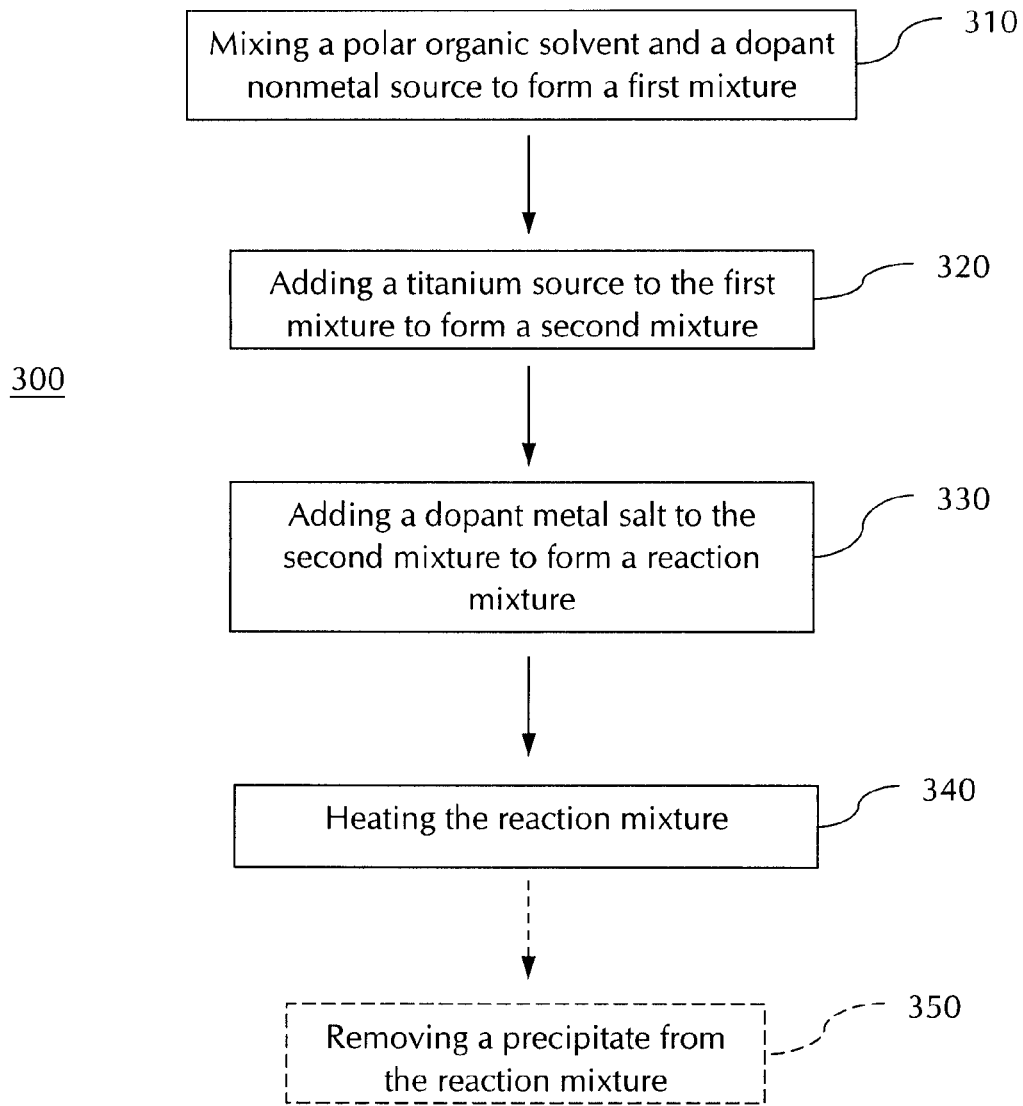
FIG. 3 depicts a method of making a quaternary oxide by a hydrothermal procedure.

FIG. 3 represents a method 300 of making a quaternary oxide by a hydrothermal procedure that includes mixing a polar organic solvent and a dopant nonmetal source to form a first mixture 310, adding a titanium source to the first mixture to form a second mixture 320, adding a dopant metal salt to the second mixture to form a reaction mixture 330, heating the reaction mixture 340, and optionally removing a precipitate from the reaction mixture 350. Adding a dopant metal salt to the second mixture may include adding water to the second mixture. Heating the reaction mixture 340 may include heating the reaction mixture in an autoclave at a temperature of from 100° C. to 350° C. for at least 4 hours. Preferably the reaction mixture is heated at a temperature of from 150° C. to 300° C. for a period of from 5 hours to 48 hours, and preferably at a temperature of from 205° C. to 250° C. for a period of at least 5 hours. After heating, the reaction mixture may include a quaternary oxide containing a dopant metal, a dopant nonmetal, titanium and oxygen.

A quaternary oxide containing a dopant metal, a dopant nonmetal, titanium and oxygen may be characterized in terms of its elemental composition. The atomic ratio of titanium to oxygen to dopant nonmetal (Ti:O:A) may be 1:0.5-1.99:0.01-1.5. Preferably the Ti:O:A atomic ratio is 1:1.0-1.99:0.01-1.0; more preferably is 1:1.5-1.99:0.01-0.5, and more preferably is 1:1.9-1.99:0.01-0.1. Preferably the dopant nonmetal is boron, carbon, nitrogen, sulfur or fluorine. More preferably the dopant nonmetal is nitrogen.

The quaternary oxide may contain the dopant metal at a concentration of at most 10 percent by weight (wt %). Preferably the quaternary oxide contains the dopant metal at a concentration of at most 5 wt %, more preferably at a concentration of at most 2 wt %. Preferably the dopant metal is calcium, cobalt, nickel, copper, gallium, strontium, yttrium, zirconium, palladium, silver, tin, lanthanum or platinum.

In addition to the elemental composition, the quaternary oxide may be characterized by a number of other properties. The crystal structure of the quaternary oxide may be characterized by X-ray diffraction, electron diffraction, neutron diffraction, electron microscopy, examination of physical and chemical properties, and/or by other well known methods. Preferably the quaternary oxide is in the anatase structure type (anatase phase). The band gap of the quaternary oxide may be characterized by spectroscopic analysis. The energy of absorbed radiation having the longest wavelength corresponds to the band gap energy. Preferably the quaternary oxide has a band gap less than 3.0 electron-volts (eV).

A catalytic composition may include the quaternary oxide containing a dopant metal, a dopant nonmetal, titanium and oxygen, where the atomic ratio of titanium to oxygen to dopant nonmetal (Ti:O:A) is 1:0.5-1.99:0.01-1.5. The catalytic composition may be characterized by the rate of conversion of a chemical reaction when the reactants of the reaction are in contact with the composition. When an organic substance is in contact with the composition and is irradiated with visible light, the concentration of the organic substance may be reduced by 40% within 4 hours. When bacteria are in contact with the composition and are irradiated with visible light, the concentration of living bacteria may be reduced by 20% within 1 hour.

The catalytic composition may be present on a support. Examples of support materials include glass, ceramic, metal, plastic and paper. The support may be porous or non-porous. Examples of porous supports include a mat of fibers, a zeolite, or a porous film. The term "on a support" includes when the composition is on at least a portion of a surface of the support. For porous supports, the term "on a support" further includes when the composition is present within the pores of the support.

Figure 4:
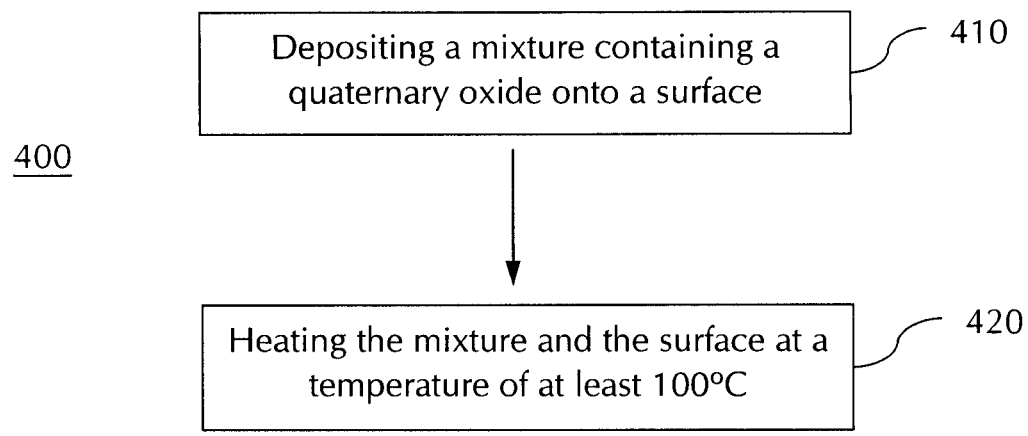
FIG. 4 depicts a method of coating a surface with a quaternary oxide.

FIG. 4 represents a method 400 of coating a surface with a quaternary oxide that includes depositing a mixture containing a quaternary oxide onto a surface 410, and heating the mixture and the surface at a temperature of at least 100° C. 420. The method may be repeated one or more times to provide a coating of the desired thickness and/or quality.

Depositing a mixture of a quaternary oxide onto a surface 410 may include combining the quaternary oxide with a liquid to provide the mixture, and applying the mixture to the surface. Depositing a mixture 410 may include applying to the surface at least a portion of a reaction mixture containing the quaternary oxide, where the reaction mixture has been prepared by a hydrothermal process. Depositing a mixture 410 also may include spinning the surface as the mixture is applied. The mixture may include other ingredients, such as a surfactant, a coupling agent or a pH buffer. Examples of other mixture ingredients include aluminum phosphate ($AlPO_4$), silane compounds such as 3-glycidoxypropyltrimethoxysilane, and fluoroalkyl-silane compounds such as (tridecafluoro-1,1,2,2-tetrahydrooctyl)-trichlorosilane.

Heating the mixture and the surface 420 may include heating in air, heating in a vacuum, or heating in an inert atmosphere. The temperature of the heating may be varied depending on factors including the surface to be coated, the heating atmosphere, the type of quaternary oxide, and the coating mixture composition. For example, a glass substrate may be coated with a quaternary oxide containing palladium, titanium, oxygen and nitrogen (Pd—Ti—O—N) by spin coating a mixture containing the quaternary oxide onto the substrate, followed by heating the coated glass in air at 400° C. for one hour. In another example, a stainless steel substrate may be coated with a Pd—Ti—O—N quaternary oxide by spin coating a mixture containing the quaternary oxide and $AlPO_4$ onto the substrate, followed by heating the coated substrate in air at 200° C. for 30 minutes. In another example, a stainless steel substrate may be coated with a Pd—Ti—O—N quaternary oxide by spin coating a mixture containing the quaternary oxide and either a silane or fluoroalkyl-silane onto the substrate, followed by heating the coated substrate in air at 140° C. for 30 minutes.

The catalytic composition may be present without a support. For example, the catalytic composition may be in the form of a powder, beads, fibers, or a porous film. The catalytic composition may also be present in one or more of these forms on a support. These forms may include nanoparticles. Nanoparticles containing titanium oxide are described, for example in U.S. Provisional Patent Application Ser. No. 60/754,680, entitled "Nanoparticles Containing Titanium Oxide", filed Dec. 29, 2005, which is incorporated by reference.

Quaternary oxides can be used in a variety of applications. Examples of possible applications include catalysis, water and air purification, gas sensing, hydrogen production, solar energy production, fiber lasers, additives for composites and fabrics, and cancer therapy. In general, any application that can utilize titanium oxide, titanium oxide doped with a metal, and/or titanium oxide doped with a nonmetal may also utilize a quaternary oxide. One advantage of quaternary oxides over these conventional materials is the high catalytic efficiency of quaternary oxides under visible light rather than UV light. Thus, applications of the conventional materials that require UV irradiation may be performed under visible light using a quaternary oxide.

Catalytic compositions including a quaternary oxide may be used to facilitate a wide variety of reactions. For example, a catalytic composition may be mixed with a reactant fluid and irradiated with visible light, providing for a chemical reaction of one or more ingredients of the fluid. The catalytic composition may then be recovered from the fluid and recycled for use in another portion of reactant fluid. Depending on the application and the composition of the dopants in the quaternary oxide, catalytic compositions containing a quaternary oxide may be used in place of general metal catalysts such as cobalt, nickel, copper, gold, iridium, lanthanum, nickel, osmium, platinum, palladium, rhodium, ruthenium, silver, strontium, yttrium, zirconium and tin.

In another example, a catalytic composition may be present on a support, and a fluid may flow in contact with the support and the composition. In this configuration, the catalytic composition may be exposed to a constant stream of fluid and does not require separation of the composition from the fluid after the reaction is performed. For example, a catalytic composition may be present on a support in an automobile exhaust system, where the exhaust system has been fitted with a visible light source, such as a fiber optic light source or an LED light source. Irradiation of the catalytic composition during operation of the automobile engine may provide for degradation of organics and other pollutants from the engine into environmentally acceptable substances.

In another example, a catalytic composition may be present on a surface that is exposed to dirt, grease and other organic and inorganic contaminants. Such a surface may be "self-cleaning" when exposed to visible light. Self-cleaning glass may have a transparent or translucent coating of a catalytic composition on one or both sides of the glass. Contaminants that contact the glass may then be degraded when the glass is exposed to visible light. It may be desirable for self-cleaning glass to have a hydrophilic surface, to provide for rinsing of any remaining degradation products from the glass with water. Examples of self-cleaning glass having surface coatings of $TiO_2$ include SunClean® glass (PPG Industries, Pittsburgh, Pa.) and Activ™ glass (Pilkington, Toledo, Ohio). A self-cleaning surface having a coating containing a quaternary oxide may also remove fingerprints from the surface automatically upon exposure to visible light.

In another example, a catalytic composition may be present on a surface that is exposed to microbes, such as bacteria and fungi, and/or to viruses. Such a surface may be a "disinfecting surface" by destroying or inactivating microbes or viruses that are present on the surface. For example, surfaces in residential, commercial or hospital environments may have a coating of a catalytic composition on the surface. Examples of surfaces that may be made into disinfecting surfaces include countertops, flooring, walls, handles, telephones, and surfaces of medical instruments.

A catalytic composition also may be applied to a surface to provide a temporary disinfection of the surface. For example, a catalytic composition may be part of a cleaning composition in the form of a liquid, a foam or a lotion. Application of the cleaning composition to a surface, followed by exposure of the surface to visible light, may cause the destruction or inactivation of microbes or viruses that are present on the surface. Such cleaning compositions may be formulated for use on skin to provide a disinfecting personal care product.

Catalytic compositions including a quaternary oxide may be used for air and/or water purification. For example, a catalytic composition may be mixed with contaminated air or water and irradiated with visible light. Contaminants in the air or water may be degraded into substances that are volatile or that are more easily separated from the fluid. For example, contaminants containing organic substances and halogenated substances may be degraded into carbon dioxide and halide ions, which may then be separated from the air or water. In the case of air purification, the degradation of contaminants may also result in control of odors in the air. Examples of water purification systems that use $TiO_2$ and UV radiation include the Photo-Cat® system (Purifics® ES Inc., London, Ontario, Calif.) and the water treatment system from Matrix Photocatalytic, Inc. (London, Ontario, Calif.). Examples of air purification systems that use $TiO_2$ and UV radiation include the air treatment system from Matrix Photocatalytic, Inc.

Quaternary oxides may be used for sensing gases. The electrical conductivity of quaternary oxides may vary depending on the chemical composition of their environment, and this variable conductivity may provide for the use of quaternary oxides to measure the type and/or amount of one or more gases. The electrical resistance of the quaternary oxide or a material containing the quaternary oxide may be measured in an environment and compared with the electrical resistance in a control environment. The difference between the measured resistance and the control resistance may be correlated with the amount and/or identity of a gas in the environment. These conductivity variations may be especially pronounced for fibers of quaternary oxides or for particles that have been sintered, and it may be desirable to use fibers or sintered materials for sensing applications. Examples of gases that may be identified and/or measured include hydrogen, carbon monoxide, hydrogen sulfide, and water. Preferably a gas sensor using a quaternary oxide can be used to sense gases at ambient conditions.

Quaternary oxides may be used for the production of hydrogen and oxygen from water. Splitting of water into hydrogen gas and oxygen gas using $TiO_2$ and UV radiation is described, for example, in T. Bak et al., *International Journal of Hydrogen Energy*, 27, 991-1022 (2002). Water may be decomposed into hydrogen and oxygen by photocatalysis with a catalytic composition containing a quaternary oxide, when irradiated with visible light. This decomposition also may be carried out in a photo-electrochemical cell having a photo-anode containing a quaternary oxide. It may be desirable to use a photo-electrochemical cell, as this can provide for separate collection of hydrogen and oxygen from the cell.

Quaternary oxides may be used for the production of electricity from solar radiation. Solar cells containing $TiO_2$ and a dye for sensitizing the $TiO_2$ are described, for example, in S. K. Deb, *Solar Energy Materials & Solar Cells*, 88, 1-10 (2005). Electric current may be produced when dye molecules are excited by exposure to light, transferring electrons into the conduction band of quaternary oxide particles. The quaternary oxide particles may conduct the electrons to a current collector that is connected to an electrical circuit with a load.

Quaternary oxide fibers may be used for fiber lasers. The quaternary oxide material may be used for one or more components of a laser, such as the laser cavity, gain medium, Bragg grating and fiber couplings. Quaternary oxides may have a direct bandgap and can thus be used to emit light.

Quaternary oxides may be used as additives in composite materials, including polymer composites, fabrics and nonwoven materials. For example, quaternary oxide fibers may be incorporated with other fibers into textile fabrics. These fabrics may provide for degradation of contaminants in contact with the fabric when exposed to visible light, resulting in self-cleaning or disinfecting fabrics. In another example, the ability to vary the composition of quaternary oxides may provide for optimized interactions of quaternary oxide particles or fibers with a composite matrix.

Quaternary oxides may be used as bioactive agents. In an aqueous environment, such as within an organism, a quaternary oxide that is irradiated with visible light may produce hydroxyl ions ($OH^-$), superoxide ions ($O_2^-$), and/or hydrogen peroxide ($H_2O_2$). A quaternary oxide that is exposed to visible light while in a cell or in contact with a cell may produce a toxic environment and damage or kill the cell. Thus, quaternary oxides may be used as anti-cancer agents when delivered to tumor cells. The use of $TiO_2$ and UV radiation as an anti-cancer agent is described, for example, in R. Cai et al., *Cancer Research*, 52, 2346-2348 (1992). It may be desirable to couple the quaternary oxide to a targeting agent that is selectively absorbed by tumor cells. Light may be delivered laparoscopically to the cells containing the quaternary oxide, resulting in cell death or a reduction in cell growth or propagation.

The following examples are provided to illustrate one or more preferred embodiments of the invention. Numerous variations may be made to the following examples that lie within the scope of the invention.

EXAMPLES

Example 1

Sol-Gel Synthesis of Pd—Ti—O—N Quaternary Oxide

Titanium tetraisopropoxide ($Ti(OCH(CH_3)_2)_4$, 14 g, reagent grade 98+%) and tetramethylammonium hydroxide ($N(CH_3)_4^+[OH^-]$, 9 g, 25% in methanol) were dissolved in 50 ml ethanol. Palladium(II) acetylacetonate ($Pd(C_5H_7O_2)_2$, 150 mg) dissolved in 2 mL dichloromethane was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH (Milwaukee, Wis.).

Example 2

Sol-Gel Synthesis of Ag—Ti—O—N Quaternary Oxide

Titanium tetraisopropoxide (10 g) and tetramethylammonium hydroxide (6 g) were dissolved in 50 ml ethanol. Silver nitrate ($AgNO_3$, 100 mg) dissolved in 2 mL water was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 3

Sol-Gel Synthesis of Y—Ti—O—N Quaternary Oxide

Titanium tetraisopropoxide (10 g) and tetramethylammonium hydroxide (7 g) were dissolved in 50 ml ethanol. Yttrium(III) acetylacetonate ($Y(C_5H_7O_2)_3$, 200 mg) dissolved in 2 mL dichloromethane was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 4

Sol-Gel Synthesis of Pt—Ti—O—N Quaternary Oxide

Titanium tetraisopropoxide (10 g) and tetramethylammonium hydroxide (6 g) were dissolved in 50 ml ethanol. Platinum(II) acetylacetonate ($Pt(C_5H_7O_2)_2$, 10 mg) dissolved in 2 mL dichloromethane was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 5

Sol-Gel Synthesis of Sr—Ti—O—N Quaternary Oxide

Titanium tetraisopropoxide (10 g) and tetramethylammonium hydroxide (6 g) were dissolved in 50 ml ethanol. Strontium carbonate ($Sr(CO_3)$, 12 mg) dissolved in 2 mL methanol was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 6

Sol-Gel Synthesis of W—Ti—O—N Quaternary Oxide

Titanium tetraisopropoxide (10 g) and tetramethylammonium hydroxide (6 g) were dissolved in 50 ml ethanol. Ammonium tungstate ($(NH_4)_x(WO4)_y$, 12 mg) dissolved in 2 mL dichloromethane was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 7

Sol-Gel Synthesis of Cu—Ti—O—N Quaternary Oxide

Titanium tetraisopropoxide (10 g) and tetramethylammonium hydroxide (6 g) were dissolved in 50 ml ethanol. Copper (II) acetylacetonate ($Cu(C_5H_7O_2)_2$, 500 mg) dissolved in 10 mL dichloromethane was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 8

Sol-Gel Synthesis of Nd—Ti—O—N Quaternary Oxide

Titanium tetraisopropoxide (10 g) and tetramethylammonium hydroxide (6 g) were dissolved in 50 ml ethanol. Neodymium(III) acetylacetonate ($Nd(C_5H_7O_2)_3$, 120 mg) dissolved in 2 mL dichloromethane was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 9

Sol-Gel Synthesis of Ni—Ti—O—N Quaternary Oxide

Titanium tetraisopropoxide (10 g) and tetramethylammonium hydroxide (6 g) were dissolved in 50 ml ethanol. Nickel (II) acetylacetonate ($Ni(C_5H_7O_2)_2$, 120 mg) dissolved in 2 mL dichloromethane was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 10

Sol-Gel Synthesis of Co—Ti—O—N Quaternary Oxide

Titanium tetraisopropoxide (10 g) and tetramethylammonium hydroxide (6 g) were dissolved in 50 ml ethanol. Cobalt (II) acetylacetonate ($Co(C_5H_7O_2)_2$, 120 mg) dissolved in 2 mL dichloromethane was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 11

Sol-Gel Synthesis of V—Ti—O—N Quaternary Oxide

Titanium tetraisopropoxide (10 g) and tetramethylammonium hydroxide (6 g) were dissolved in 50 ml ethanol. Vanadium(III) acetylacetonate ($V(C_5H_7O_2)_3$, 120 mg) dissolved in 2 mL dichloromethane was mixed with 20 mL water, and this mixture was added to the ethanol solution gradually. The reaction mixture was maintained at 70° C. for 12 hours. The precipitate from the reaction mixture was removed, washed with water, and calcined at 500° C. for 3 hours. All reagents and solvents were obtained from ALDRICH.

Example 12

Hydrothermal Synthesis of Ti—O—N Ternary Oxide

Ethylene glycol ($HO—CH_2—CH_2—OH$, 50 mL) was dried at 140° C. for 1 hour with vigorous stirring in a flask under a nitrogen atmosphere. Ethylene diamine ($NH_2—CH_2—CH_2—NH_2$, 5 mL) was dehydrated with $MgSO_4$ and added to the ethylene glycol. The mixture was stirred for 5 minutes, and then titanium tetraisopropoxide (5 mL) was added, followed by stirring for an additional 5 minutes. Deionized water (2 mL) was added to the mixture, and the reaction mixture was then transferred to a poly(tetrafluoroethylene)-lined stainless steel autoclave. The reaction mixture was heated to a temperature of 205-250° C. for 5-12 hours, and then cooled to room temperature. The precipitate from the reaction mixture was filtered and washed three times with ethanol. All reagents and solvents were obtained from ALDRICH.

Example 13

Hydrothermal Synthesis of Pd—Ti—O—N Quaternary Oxide

Ethylene glycol (50 mL) was dried at 140° C. for 1 hour with vigorous stirring in a flask under a nitrogen atmosphere. Ethylene diamine (5 mL) was dehydrated with $MgSO_4$ and added to the ethylene glycol. The mixture was stirred for 5 minutes, and then titanium tetraisopropoxide (5 mL) was added, followed by stirring for an additional 5 minutes. Deionized water (2 mL) and a solution of palladium(II) acetylacetonate ($Pd(C_5H_7O_2)_2$, 50 mg) in 2 mL dichloromethane were added to the mixture, and the reaction mixture was then transferred to a poly(tetrafluoroethylene)-lined stainless steel autoclave. The reaction mixture was heated to a temperature of 205-250° C. for 5-12 hours, and then cooled to room temperature. The precipitate from the reaction mixture was filtered and washed three times with ethanol. All reagents and solvents were obtained from ALDRICH.

Example 14

Hydrothermal Synthesis of Ag—Ti—O—N Quaternary Oxide

Ethylene glycol (50 mL) was dried at 140° C. for 1 hour with vigorous stirring in a flask under a nitrogen atmosphere. Ethylene diamine (5 mL) was dehydrated with $MgSO_4$ and added to the ethylene glycol. The mixture was stirred for 5 minutes, and then titanium tetraisopropoxide (5 mL) was added, followed by stirring for an additional 5 minutes. Silver nitrate ($AgNO_3$, 100 mg) dissolved in 2 mL deionized water was added to the mixture, and the reaction mixture was then transferred to a poly(tetrafluoroethylene)-lined stainless steel autoclave. The reaction mixture was heated to a temperature of 205-250° C. for 5-12 hours, and then cooled to room temperature. The precipitate from the reaction mixture was filtered and washed three times with ethanol. All reagents and solvents were obtained from ALDRICH.

Example 15

Quaternary Oxide Surface Coating On Glass

A Pd—Ti—O—N quaternary oxide was made by the procedure of Example 13, except that the precipitate was not removed after the autoclave reaction. The suspension was coated onto a clean glass substrate by spin-coating. The substrate was rotated at 1,000 revolutions per minute (rpm) for 10 seconds. The coated glass was then calcined in air for 1 hour at 400° C., with a heating rate of 2° C./min. The thickness of the coating was approximately 5 micrometers ($\mu m$), as measured by scanning electron microscopy (SEM).

Example 16

Quaternary Oxide Surface Coating On Stainless Steel

A Pd—Ti—O—N quaternary oxide was made by the procedure of Example 13, except that the precipitate was not removed after the autoclave reaction. The suspension was separated with a centrifuge to isolate nanofibers of the Pd—Ti—O—N quaternary oxide. Approximately 1 g of the fibers were dispersed in 30 mL of ethanol, and a solution of a coupling agent in ethanol was added to form a coating mixture. The coating mixture was coated onto a stainless steel substrate by spin-coating. The substrate was rotated at 500 rpm for 10 seconds. The coated stainless steel was then calcined in air for 30 minutes. The spin-coating and calcining were repeated 3 times.

Three different coupling agent solutions were examined for the stainless steel coatings:

(a) An aluminum phosphate ($AlPO_4$) solution was prepared by dissolving 4 g $Al(NO_3)_3 \cdot 9 H_2O$ and 0.5 g $P_2O_5$ in 20 mL ethanol. The calcining for the surface using this agent was performed at 200° C.

(b) A silane compound solution was prepared by dissolving 3-glycidoxy-propyltrimethoxysilane in ethanol to provide 10 mL of a 2% solution. The calcining for the surface using this agent was performed at 140° C.

(c) A fluoroalkyl-silane compound solution was prepared by dissolving tridecafluoro-1,1,2,2-tetrahydrooctyl)-trichlorosilane in ethanol provide 10 mL of a 2% solution. The calcining for the surface using this agent was performed at 140° C.

Example 17

Disinfecting Surfaces

A stainless steel surface coated with a quaternary oxide as described in Example 16 was treated with a culture of bacteria. The surface was then irradiated with visible light, and the percentage of surviving cells was measured over time. The bacteria examined were either *Escherichia coli* (*E. coli*), *Pseudomonas aeruginosa* (*P. aeruginosa*), *Staphylococcus aureus* (*S. aureus*), or *bacillus* spores.

Figure 5:
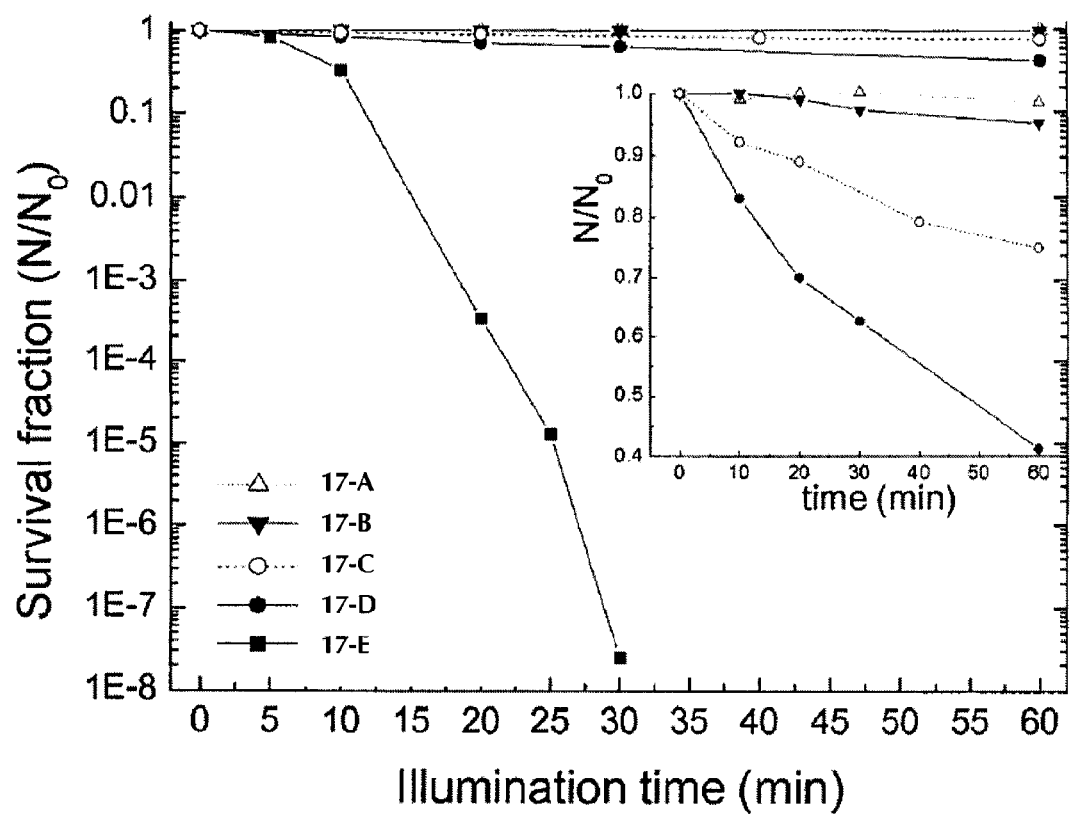
FIG. 5 is a graph of bacteria survival fraction versus time for *Escherichia coli* (*E. coli*) on coated and uncoated stainless steel surfaces.

FIG. 5 is a graph of bacteria survival versus time for *E. coli* on stainless steel surfaces. Surface 17-A was a control surface with no oxide coating. Surface 17-B had a coating of anatase $TiO_2$ fibers. Surface 17-D had a coating of Ti—O—N. Surfaces 17-C and 17-E each had a coating of Pd—Ti—O—N. Each of the surfaces was exposed to visible light, except for surface 17-C. The surface coated with quaternary oxide and exposed to visible light exhibited the largest reduction in the amount of living bacteria compared to the other surfaces. For this surface, 70% of the bacteria were killed after 10 minutes of exposure, and over 99% of the bacteria were killed after 20 minutes of exposure. The surface coated with Pd—Ti—O—N quaternary oxide but not exposed to visible light also exhibited disinfecting properties, with 15-20% of the bacteria killed after 10 minutes of exposure, and almost 60% of the bacteria killed after 60 minutes exposure.

Figure 6:
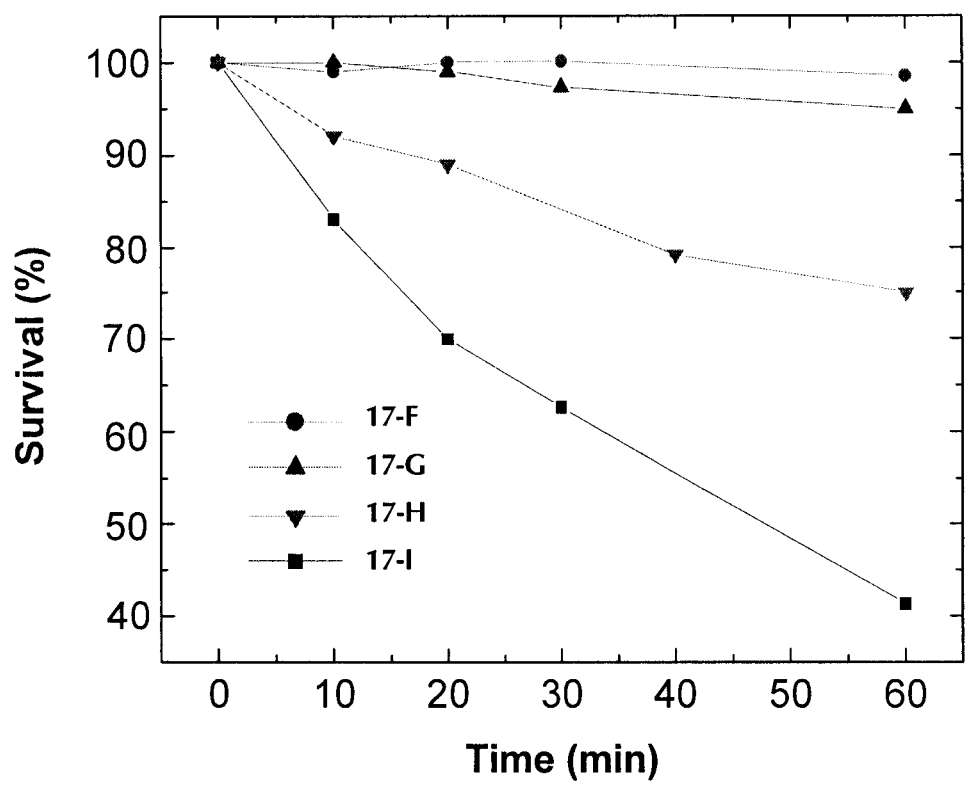
FIG. 6 is a graph of bacteria survival percentage versus time for *E. coli* on coated and uncoated stainless steel surfaces.

FIG. 6 is a graph of bacteria survival versus time for *E. coli* on stainless steel surfaces. Surface 17-F was a control surface with no oxide coating, and surface 17-G had a coating of anatase $TiO_2$ fibers. Surfaces 17-H and 17-I each had a coating of Ag—Ti—O—N. Each of the surfaces was exposed to visible light, except for surface 17-H. The surface coated with quaternary oxide and exposed to visible light exhibited the largest reduction in the amount of living bacteria compared to the other surfaces. For this surface, 15-20% of the bacteria were killed after 10 minutes of exposure, and almost 60% of the bacteria were killed after 60 minutes of exposure. The surface coated with Ag—Ti—O—N quaternary oxide but not exposed to visible light also exhibited disinfecting properties, with almost 10% of the bacteria killed after 10 minutes of exposure, and 20-25% of the bacteria killed after 60 minutes exposure.

Figure 7:
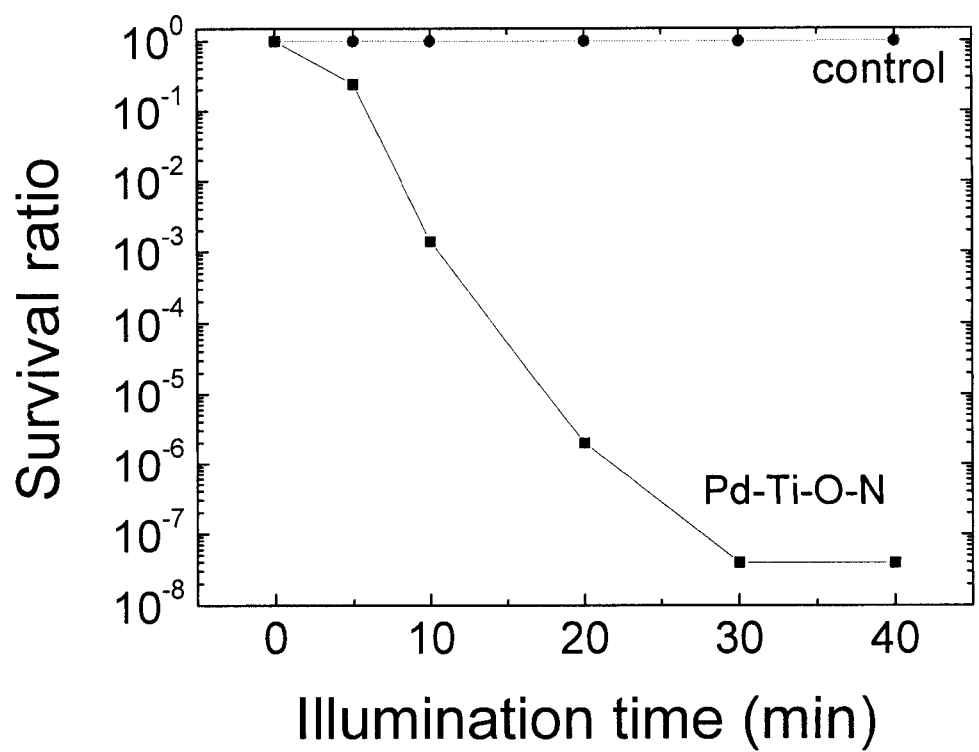
FIG. 7 is a graph of bacteria survival ratio versus time on coated and uncoated stainless steel surfaces for *Pseudomonas aeruginosa*.
Figure 8:
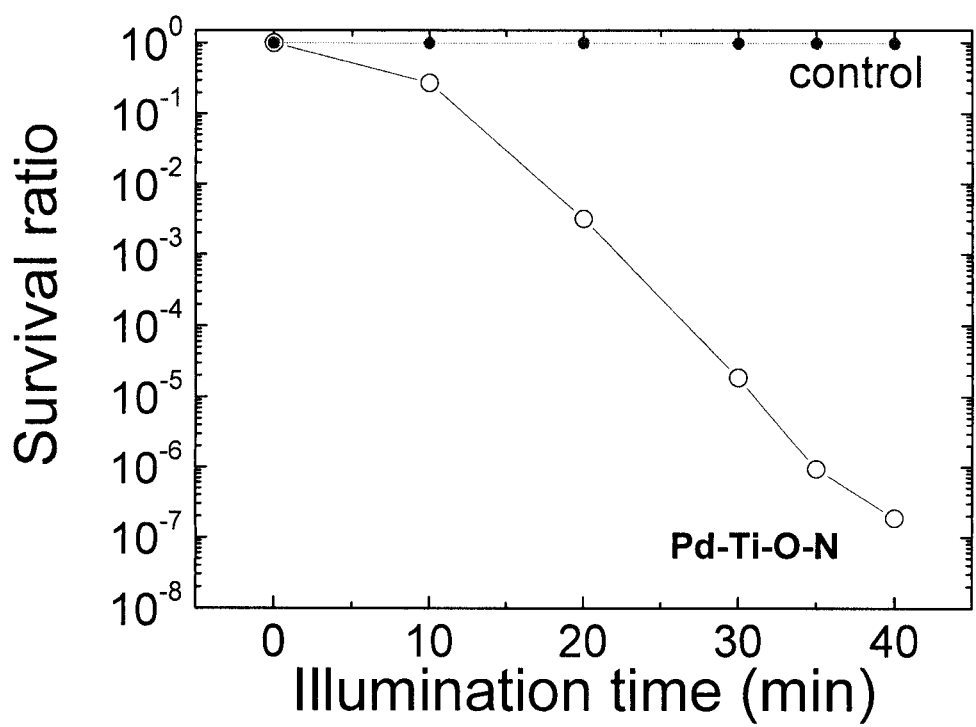
FIG. 8 is a graph of bacteria survival ratio versus time on coated and uncoated stainless steel surfaces for *Staphylococcus aureus*.

FIGS. 7 and 8 are graphs of bacteria survival versus time on stainless steel surfaces exposed to visible light for *P. aeruginosa* (FIG. 7) and *S. aureus* (FIG. 8). A Pd—Ti—O—N quaternary oxide coating was disinfecting for each type of bacteria.

Example 18

Self-Cleaning Surfaces

Figure 9:
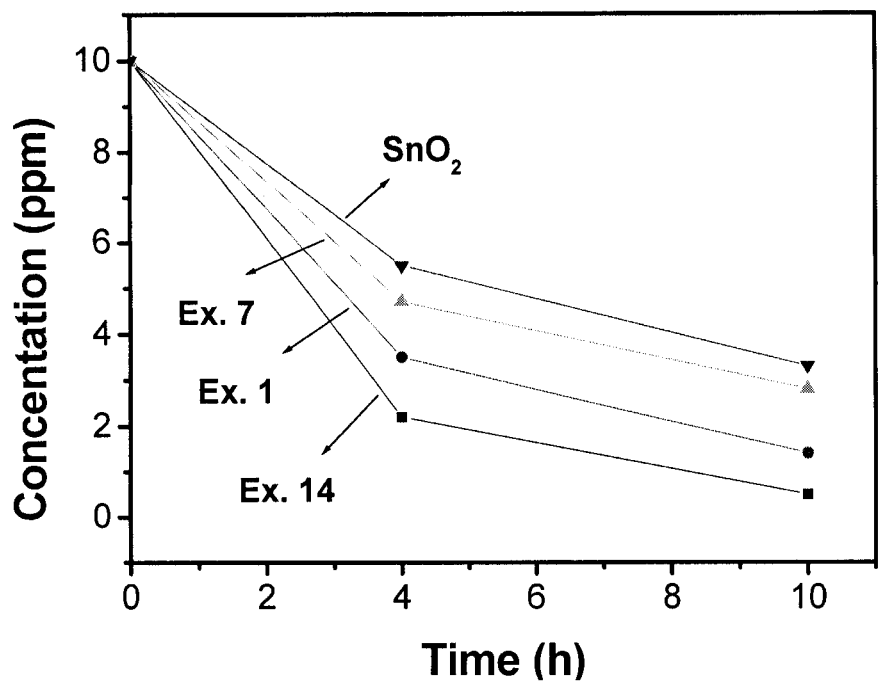
FIG. 9 is a graph of methylene blue concentration versus time for a variety of coated surfaces.
Figure 10:
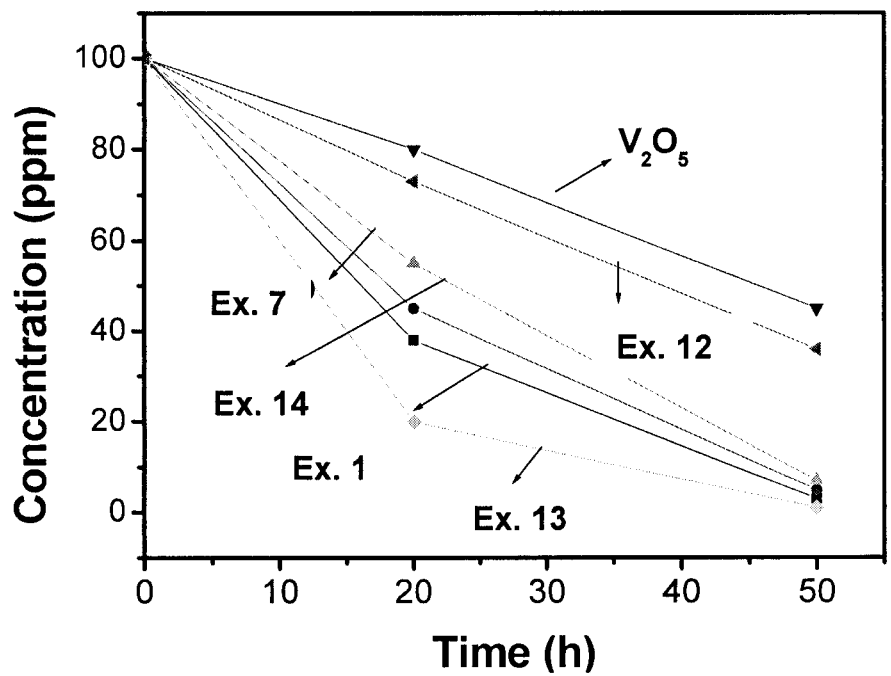
FIG. 10 is a graph of humic acid concentration versus time for a variety of coated surfaces.
Figure 11A:
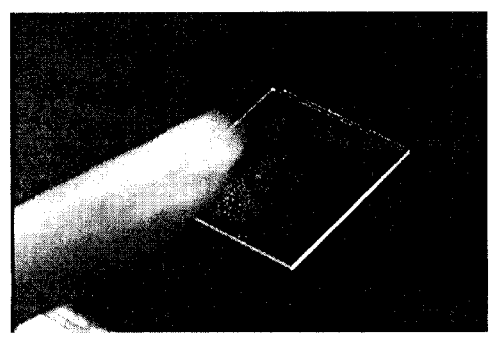
FIG. 11A-FIG. 11D are a sequence of images for a fingerprint on a glass slide coated with a quaternary oxide.
Figure 11B:
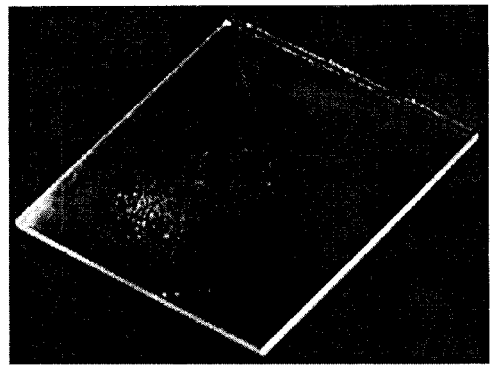
Figure 11C:
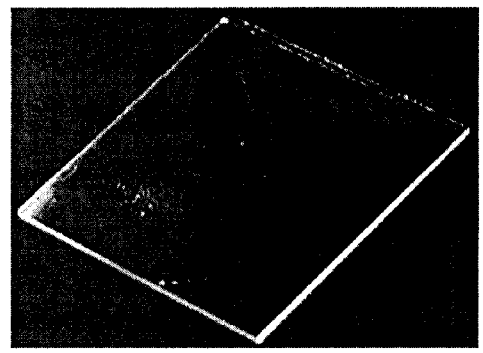
Figure 11D:
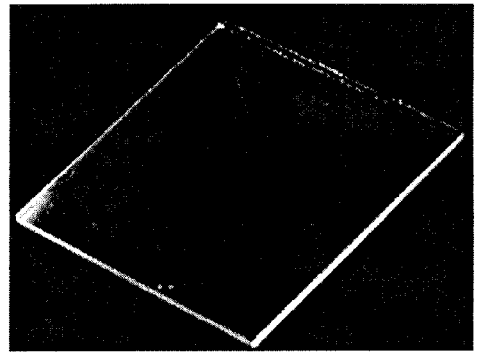

A stainless steel surface coated with a quaternary oxide as described in Example 16 was treated with an organic substance. The surface was then irradiated with visible light, and the concentration of organic material was measured over time. FIG. 9 is a graph of methylene blue concentration versus time for a variety of coated surfaces. The data labeled "$SnO_2$" was for a surface coated with $SnO_2$, and the remainder of the data corresponds to surfaces coated with the quaternary oxides from Examples 1, 7 and 14. FIG. 10 is a graph of humic acid concentration versus time for a variety of coated surfaces. The data labeled "$V_2O_5$" was for a surface coated with $V_2O_5$, and the remainder of the data corresponds to surfaces coated with the quaternary oxides from Examples 1, 7, 13 and 14 or with the ternary oxide from Example 12.

Example 19

Automatic Fingerprint Removal From Surfaces

The Pd—Ti—O—N coated surfaces of Example 15 (glass) and Example 16 (stainless steel) were touched with a human finger to deposit a fingerprint. The surfaces were exposed to visible light and monitored for the presence of the fingerprint residue over time. FIGS. 11A-11D are a sequence of images for a glass slide coated with Pd—Ti—O—N. The fingerprint was visibly undetectable within 0.6 seconds of its deposit on the slide.

Example 20

Gas Sensing

Figure 12:
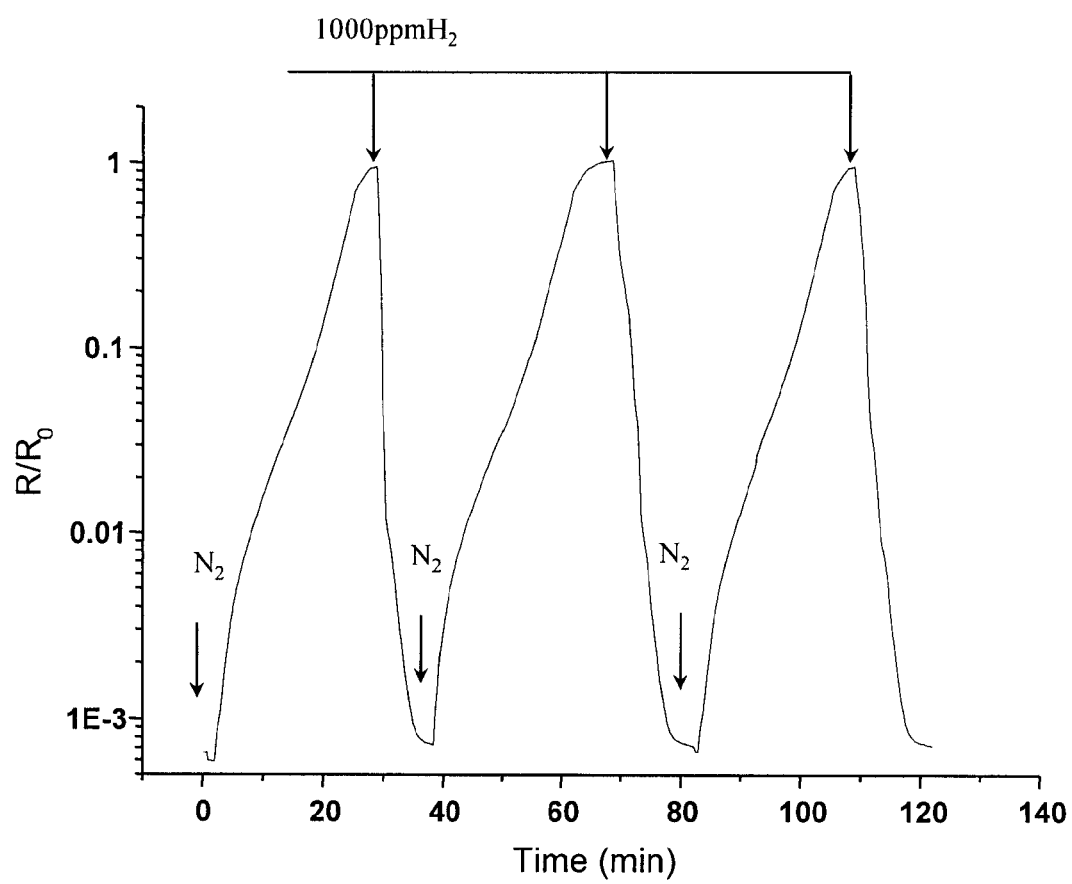
FIG. 12 is a graph of normalized resistance over time for quaternary oxide nanofibers, with alternate introduction of a nitrogen gas stream and a gas stream containing 1,000 ppm hydrogen.
Figure 13:
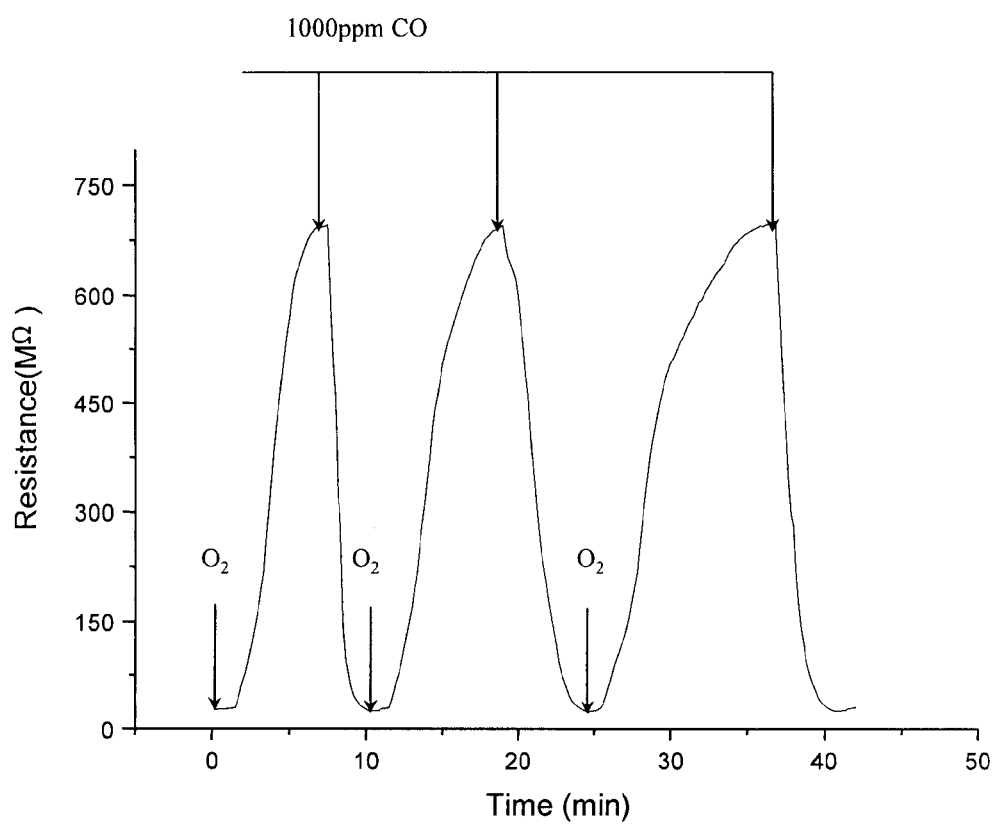
FIG. 13 is a graph of resistance over time for quaternary oxide nanofibers, with alternate introduction of an oxygen gas stream and a gas stream containing 1,000 ppm carbon monoxide.

Nanofibers of Pd—Ti—O—N were connected to an ohmmeter and exposed to a variety of gases. The resistance of the fibers increased by 2-3 orders of magnitude when exposed to oxidizable gases such as hydrogen and carbon monoxide. FIG. 12 is a graph of normalized resistance over time, noting the alternate introduction of a nitrogen gas stream (N2) and a gas stream containing 1,000 ppm hydrogen. The resistance measurements were carried out at 100° C. FIG. 13 is a graph of resistance over time, noting the alternate introduction of an oxygen gas stream ($O_2$) and a gas stream containing 1,000 ppm carbon monoxide. The resistance measurements were carried out at 200° C.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of making a catalytic composition, comprising:
    combining ingredients to form a reaction mixture, the ingredients comprising a titanium source, a dopant nonmetal source comprising at least one nonmetal selected from the group consisting of boron, nitrogen, sulfur and fluorine, a metal salt different from the dopant nonmetal source and not including titanium, and a polar organic solvent; and
    heating the reaction mixture to form a catalytic composition comprising titanium, the metal other than titanium, the dopant nonmetal, and oxygen.

2. The method of claim 1, where the titanium source is selected from the group consisting of titanium(IV) halide, titanium(IV) alkoxide, titanium(IV) nitrate, and titanium(IV) oxysulfate.

3. The method of claim 1, where the metal salt comprises an ion of a metal selected from the group consisting of calcium, cobalt, nickel, copper, gallium, strontium, yttrium, zirconium, palladium, silver, tin, lanthanum and platinum.

4. The method of claim 1, where the heating comprises maintaining the reaction mixture at a temperature of from 50° C. to 250° C. for a period of at least 4 hours.

5. The method of claim 4, where the combining comprises mixing the titanium source and the dopant nonmetal source with the polar organic solvent to form a first mixture, and adding the metal salt to the first mixture.

6. The method of claim 5, further comprising adding water to the first mixture.

7. The method of claim 4, further comprising removing a precipitate from the reaction mixture after the heating.

8. The method of claim 7, further comprising calcining the precipitate.

9. The method of claim 1, where the heating comprises maintaining the reaction mixture at a temperature of from 100° C. to 350° C. for a period of at least 4 hours.

10. The method of claim 9, where the heating is performed in an autoclave.

11. The method of claim 9, where the combining comprises:
    mixing the polar organic solvent with the dopant nonmetal source to form a first mixture;
    adding the titanium source to the first mixture to form a second mixture; and
    adding the metal salt to the second mixture.

12. The method of claim 11, further comprising adding water to the second mixture.

13. The method of claim 9, further comprising removing a precipitate from the reaction mixture after the heating.

14. A method of making a catalytic composition, the method comprising:
    combining a titanium source and a dopant nonmetal source comprising at least one nonmetal selected from the group consisting of boron, nitrogen, sulfur and fluorine with a polar organic solvent to form a first mixture;
    adding a metal salt different from the dopant nonmetal source and not including titanium to the first mixture to form a reaction mixture;
    heating the reaction mixture at a temperature of from 50° C. to 250° C. for a period of at least 4 hours;
    removing a precipitate from the reaction mixture; and
    calcining the precipitate, thereby forming a catalytic composition comprising titanium, the metal other than titanium, the dopant nonmetal, and oxygen.

15. The method of claim 14, further comprising adding water to the first mixture.

16. The method of claim 14, where
    the titanium source is selected from the group consisting of titanium(IV) halide, titanium(IV) alkoxide, titanium(IV) nitrate, and titanium(IV) oxysulfate; and
    the metal salt comprises an ion of a metal selected from the group consisting of calcium, cobalt, nickel, copper, gallium, strontium, yttrium, zirconium, palladium, silver, tin, lanthanum and platinum.

17. A method of making a catalytic composition, comprising:
- combining a polar organic solvent with a dopant nonmetal source comprising at least one nonmetal selected from the group consisting of boron, nitrogen, sulfur and fluorine to form a first mixture;
- adding a titanium source to the first mixture to form a second mixture;
- adding a metal salt different from the dopant nonmetal source and not including titanium to the second mixture to form a reaction mixture; and
- heating the reaction mixture in an autoclave at a temperature of from 100° C. to 350° C. for a period of at least 4 hours to form a catalytic composition comprising titanium, the metal other than titanium, the dopant nonmetal, and oxygen.

18. The method of claim 17, further comprising adding water to the second mixture.

19. The method of claim 17, where
- the titanium source is selected from the group consisting of titanium(IV) halide, titanium(IV) alkoxide, titanium(IV) nitrate, and titanium(IV) oxysulfate; and
- the metal salt comprises an ion of a metal selected from the group consisting of calcium, cobalt, nickel, copper, gallium, strontium, yttrium, zirconium, palladium, silver, tin, lanthanum and platinum.

* * * * *